US006344436B1

(12) United States Patent
Smith et al.

(10) Patent No.: US 6,344,436 B1
(45) Date of Patent: Feb. 5, 2002

(54) LIPOPHILIC PEPTIDES FOR MACROMOLECULE DELIVERY

(75) Inventors: Louis C. Smith; James T. Sparrow; Jochen Hauer; Martha P. Mims, all of Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 08/584,043

(22) Filed: Jan. 8, 1996

(51) Int. Cl.$^7$ .............................................. C07K 14/00

(52) U.S. Cl. .......................... 514/2; 530/345; 530/359; 530/402

(58) Field of Search .............................. 574/2; 530/345, 530/359, 402

(56) References Cited

U.S. PATENT DOCUMENTS

| 5,108,921 A | | 4/1992 | Low et al. |
| 5,364,791 A | | 11/1994 | Vegeto et al. |
| 5,631,237 A | * | 5/1997 | Dzau et al. ................... 514/44 |

FOREIGN PATENT DOCUMENTS

| WO | 8702061 | 4/1987 |
| WO | 9210512 | 6/1992 |
| WO | 9318759 | 9/1993 |
| WO | 9521931 | 8/1995 |
| WO | 9640958 | 12/1996 |

OTHER PUBLICATIONS

Dryer et al., "Structural features of synthetic peptides of apolipoprotein E that bind the LDL receptor," *Journal of Lipid Research* 36(1):80–88 (1995).
Gottschalk et al., "A novel DNA–peptide complex for efficient gene transfer and expression in mammalian cells," *Gene Therapy* 3:448–457 (1996).
Mims et al., "A non–exchangeable and peptide capable of mediating binding to the LDL receptor," *Circulation* 86(4):I–551 at abstract No. 2193 (1992).
Subbarao et al., "ph–Dependent Bilayer Destabilization by an Amphipathic Peptide," *Biochemistry* 26:2964–2979 (1987).
Wagner et al., "Influenza virus hemagglutinin HA–2–terminal fusogenic peptides augment gene transfer by transferrin–polylysine–DNA complexes: Toward a synthetic virus–like gene–tranfer vehicle," *Proc. Natl. Acad. Sci. USA* 89:7934–7938 (1992).
Weitman et al., "Cellular Localization of the Folate Receptor: Potential Role in Drug Toxicity and Folate Homeostasis[1]," *Cancer Research* 52:6708–7611 (1992).
Weitman et al., "Distribution of the Folate Receptor GP38 in Normal and Malignant Cell Lines and Tissues," *Cancer Research* 52:3396–3401 (1992).
Wharton et al., "Membrane Fusion by Peptide Analogues of Influenza Virus Haemagglutinin," *J. Gen. Virol.* 69:1847–1857 (1988).
Wu et al., "Receptor–Mediated Gene Delivery In Vivo," *J. Biol. Chem.* 266:14338–14342 (1991).
Wu et al., "Targeting Genes: Delivery and Persistent Expression of a Foreign Gene Driven by Mammalian Regulatory Elements In Vivo," *J. Biol. Chem.* 264:16985–16987 (1989).
Wu and Wu, "Receptor–Medicated Gene Delivery and Expression In Vivo," *J. Biol. Chem.* 263:14621–14624 (1988).
Wu and Wu, "Evidence for Targeted Gene Delivery to Hep G2 Hepatoma Cells In Vitro," *Biochemistry* 27:887–892 (1988).
Wu and Wu, "Receptor–mediated In Vitro Gene Transformation by a Soluble DNA Carrier System," *J. Biol. Chem.* 262:4429–4432 (1987).
Zenke et al., "Receptor–Mediated Endocytosis of Transferrin–Polycation Conjugates: An Efficient Way to Introduce DNA Into Hematopoietic Cells," *Proc. Natl. Acad. Sci. USA* 87:3655–3659 (1990).
Anderson, "Human Gene Therapy," *Science* 256:808–813 (1992).
Campbell et al. "Folate–binding Protein is a Marker for Ovarian Cancer," *Cancer Research* 51:5329–5338 (1991).
Coney et al., "Cloning of a Tumor–associated Antigen: MOv18 and MOv19 Antibodies Recognize a Folate–binding Protein," *Cancer Research* 51:6125–6132 (1991).
Cotten et al., "Transferrin–polycation–mediated Introduction of DNA Into Human Leukemic Cells: Stimulation by Agents That Affect the Survival of Tranfected DNA or Modulate Transferring Receptor Levels," *Proc. Natl. Acad. Sci. USA* 87:4033–4037 (1990).
Doms et al., "Ch. 15 —Influenza Virus Hemagglutinin and Membrane Fusion," in *Membrane Fusion* pp. 313–335, Marcel Dekker, Inc., New York (1991).
Gilardi et al., "Expression of Human x1–Antitrypsin Using a Recombinant Adenovirus Vector," *Federation of European Biochemical Societies* 267:60–62 (1990).
Leamon and Low, "Cytotoxicity of Momordin–Folate Conjugates in Cultured Human Cells," *J. Biol. Chem.* 267:24966–24971 (1992).

(List continued on next page.)

Primary Examiner—Karen Cochrane Carlson
Assistant Examiner—Stephen Tu
(74) Attorney, Agent, or Firm—Lyon & Lyon LLP

(57) ABSTRACT

Peptide-macromolecule complexes for delivery of nucleic acid to a cell. The nucleic acid carrier includes a binding complex. The binding complex contains a binding moiety which noncovalently binds to the nucleic acid. The binding complex can also contain a binding moiety which is associated with a surface ligand, nuclear ligand or a lysis agent. These may be associated with the binding moiety by spacers. In addition, the carrier may include a nucleic acid with a combination of the above binding complexes or binding moieties.

14 Claims, 6 Drawing Sheets-

OTHER PUBLICATIONS

Leamon and Low, "Delivery of Macromolecules into Living Cells: A Method That Exploits Folate Receptor Endocytosis," *Proc. Natl. Acad. Sci. USA* 88:5572–5576 (1991).

Liu and Huang, "ph–sensitive, plasma–stable liposomes with relatively prolonged residence in circulation, " *Biochem. Biophys. Acta* 1022:348–354 (1990).

Mims et al., "A Nonexchangeable Apolipoprotein E Peptide That Mediates Binding to the Low Density Lipoprotein Receptor," *J. Biol. Chem.* 269:20539–20547 (1994).

Morgan and Anderson, "Human Gene Therapy," *Ann. Rev. Biochem.* 62:191–217 (1993).

Ojcius and Young, "Cytolytic pore–forming proteins and peptides: is there a common structure motif?" *TIBS* 16:225–229 (1991).

Rosenfeld et al., "Adenovirus–Mediated Transfer of a Recombinant α1–Antitrypsin Gene to the Lung Epithelium in Vivo," *Science* 252:431–434 (1991).

Stratford–Perricaudet et al., "Evaluation of the Transfer and Expression in Mice of an Enzyme–Encoding Gene Using a Human Adenovirus Vector," *Human Gene Therapy* 1:241–256 (1990).

\* cited by examiner

A PEPTIDE-BASED LIPOSOMAL DNA DELIVERY SYSTEM

LIPOPHILIC PEPTIDE LIGAND FOR LDL RECEPTOR distearyl-glycyl-apoE-3 129-169

```
                         SEQUENCE LISTING (1) GENERAL INFORMATION:

(iii) NUMBER OF SEQUENCES:        139

(2) INFORMATION FOR SEQ ID NO:  1:

(i) SEQUENCE CHARACTERISTICS:
          (A) LENGTH:                9 amino acids
          (B) TYPE:                  amino acid
          (C) STRANDEDNESS:          single
          (D) TOPOLOGY:              linear (ii) MOLECULE TYPE:              peptide (xi) SEQUENCE DESCRIPTION: SEQ ID NO:  1:

Arg Lys Leu Arg Lys Arg Leu Leu Arg
 1               5

(2) INFORMATION FOR SEQ ID NO:  2:

(i) SEQUENCE CHARACTERISTICS:
          (A) LENGTH:                8 amino acids
          (B) TYPE:                  amino acid
          (C) STRANDEDNESS:          single
          (D) TOPOLOGY:              linear (ii) MOLECULE TYPE:              peptide (xi) SEQUENCE DESCRIPTION: SEQ ID NO:  2:

Lys Lys Lys Lys Lys Val Thr Lys
 1               5

(2) INFORMATION FOR SEQ ID NO:  3:
```

```
        (i) SEQUENCE CHARACTERISTICS:
             (A) LENGTH:              9 amino acids
             (B) TYPE:                amino acid
             (C) STRANDEDNESS:        single
             (D) TOPOLOGY:            linear (ii) MOLECULE TYPE:           peptide (xi) SEQUENCE DESCRIPTION: SEQ ID NO:  3:

Lys Lys Lys Lys Lys Lys Val Thr Lys
1               5

(2) INFORMATION FOR SEQ ID NO:  4:

(i) SEQUENCE CHARACTERISTICS:
             (A) LENGTH:              10 amino acids
             (B) TYPE:                amino acid
             (C) STRANDEDNESS:        single
             (D) TOPOLOGY:            linear (ii) MOLECULE TYPE:           peptide (xi) SEQUENCE DESCRIPTION: SEQ ID NO:  4:

Lys Lys Lys Lys Lys Lys Lys Val Thr Lys
1               5                  10

(2) INFORMATION FOR SEQ ID NO:  5:

(i) SEQUENCE CHARACTERISTICS:
             (A) LENGTH:              11 amino acids
             (B) TYPE:                amino acid
             (C) STRANDEDNESS:        single
             (D) TOPOLOGY:            linear (ii) MOLECULE TYPE:           peptide (xi) SEQUENCE DESCRIPTION: SEQ ID NO:  5:

Lys Lys Lys Lys Lys Lys Lys Lys Val Thr Lys
1               5                  10

(2) INFORMATION FOR SEQ ID NO:  6:

(i) SEQUENCE CHARACTERISTICS:
             (A) LENGTH:              12 amino acids
             (B) TYPE:                amino acid
             (C) STRANDEDNESS:        single
             (D) TOPOLOGY:            linear (ii) MOLECULE TYPE:           peptide (xi) SEQUENCE DESCRIPTION: SEQ ID NO:  6:

Lys Lys Lys Lys Lys Lys Lys Lys Lys Val Thr Lys
1               5                  10

(2) INFORMATION FOR SEQ ID NO:  7:

(i) SEQUENCE CHARACTERISTICS:
             (A) LENGTH:              13 amino acids
             (B) TYPE:                amino acid
             (C) STRANDEDNESS:        single
             (D) TOPOLOGY:            linear (ii) MOLECULE TYPE:           peptide (xi) SEQUENCE DESCRIPTION: SEQ ID NO:  7:

Lys Lys Lys Lys Lys Lys Lys Lys Lys Lys Val Thr Lys
1               5                  10

(2) INFORMATION FOR SEQ ID NO:  8:
```

```
        (i) SEQUENCE CHARACTERISTICS:
             (A) LENGTH:              14 amino acids
             (B) TYPE:                amino acid
             (C) STRANDEDNESS:        single
             (D) TOPOLOGY:            linear (ii) MOLECULE TYPE:            peptide (xi) SEQUENCE DESCRIPTION: SEQ ID NO: 8:

Lys Lys Lys Lys Lys Lys Lys Lys Lys Lys Lys Val Thr Lys
1               5                   10

(2) INFORMATION FOR SEQ ID NO: 9:

(i) SEQUENCE CHARACTERISTICS:
             (A) LENGTH:              15 amino acids
             (B) TYPE:                amino acid
             (C) STRANDEDNESS:        single
             (D) TOPOLOGY:            linear (ii) MOLECULE TYPE:            peptide (xi) SEQUENCE DESCRIPTION: SEQ ID NO: 9:

Lys Lys Lys Lys Lys Lys Lys Lys Lys Lys Lys Lys Val Thr Lys
1               5                   10                  15

(2) INFORMATION FOR SEQ ID NO: 10:

(i) SEQUENCE CHARACTERISTICS:
             (A) LENGTH:              16 amino acids
             (B) TYPE:                amino acid
             (C) STRANDEDNESS:        single
             (D) TOPOLOGY:            linear (ii) MOLECULE TYPE:            peptide (xi) SEQUENCE DESCRIPTION: SEQ ID NO: 10:

Lys Lys Lys Lys Lys Lys Lys Lys Lys Lys Lys Lys Lys Val Thr Lys
1               5                   10                  15

(2) INFORMATION FOR SEQ ID NO: 11:

(i) SEQUENCE CHARACTERISTICS:
             (A) LENGTH:              17 amino acids
             (B) TYPE:                amino acid
             (C) STRANDEDNESS:        single
             (D) TOPOLOGY:            linear (ii) MOLECULE TYPE:            peptide (xi) SEQUENCE DESCRIPTION: SEQ ID NO: 11:

Lys Lys Lys Lys Lys Lys Lys Lys Lys Lys Lys Lys Lys Lys Val Thr
1               5                   10                  15

Lys (2) INFORMATION FOR SEQ ID NO: 12:

(i) SEQUENCE CHARACTERISTICS:
             (A) LENGTH:              18 amino acids
             (B) TYPE:                amino acid
             (C) STRANDEDNESS:        single
             (D) TOPOLOGY:            linear (ii) MOLECULE TYPE:            peptide (xi) SEQUENCE DESCRIPTION: SEQ ID NO: 12:

Lys Lys Lys Lys Lys Lys Lys Lys Lys Lys Lys Lys Lys Lys Lys Val
1               5                   10                  15
```

Thr Lys (2) INFORMATION FOR SEQ ID NO: 13:

(i) SEQUENCE CHARACTERISTICS:
        (A) LENGTH:           19 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 13:

Lys Lys Lys Lys Lys Lys Lys Lys Lys Lys Lys Lys Lys Lys Lys
1               5                   10                  15

Val Thr Lys (2) INFORMATION FOR SEQ ID NO: 14:

(i) SEQUENCE CHARACTERISTICS:
        (A) LENGTH:           20 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 14:

Lys Lys Lys Lys Lys Lys Lys Lys Lys Lys Lys Lys Lys Lys Lys
1               5                   10                  15

Lys Val Thr Lys
        20

(2) INFORMATION FOR SEQ ID NO: 15:

(i) SEQUENCE CHARACTERISTICS:
        (A) LENGTH:           21 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 15:

Lys Lys Lys Lys Lys Lys Lys Lys Lys Lys Lys Lys Lys Lys Lys
1               5                   10                  15

Lys Lys Val Thr Lys
            20

(2) INFORMATION FOR SEQ ID NO: 16:

(i) SEQUENCE CHARACTERISTICS:
        (A) LENGTH:           22 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 16:

Lys Lys Lys Lys Lys Lys Lys Lys Lys Lys Lys Lys Lys Lys Lys
1               5                   10                  15

Lys Lys Lys Val Thr Lys
            20

(2) INFORMATION FOR SEQ ID NO: 17:

(i) SEQUENCE CHARACTERISTICS:
        (A) LENGTH:                   23 amino acids
        (B) TYPE:                     amino acid
        (C) STRANDEDNESS:        single
        (D) TOPOLOGY:             linear (ii) MOLECULE TYPE:         peptide (xi) SEQUENCE DESCRIPTION: SEQ ID NO: 17:

Lys Lys Lys Lys Lys Lys Lys Lys Lys Lys Lys Lys Lys Lys Lys
1           5                10             15

Lys Lys Lys Lys Val Thr Lys
       20

(2) INFORMATION FOR SEQ ID NO: 18:

(i) SEQUENCE CHARACTERISTICS:
        (A) LENGTH:                   24 amino acids
        (B) TYPE:                     amino acid
        (C) STRANDEDNESS:        single
        (D) TOPOLOGY:             linear (ii) MOLECULE TYPE:         peptide (xi) SEQUENCE DESCRIPTION: SEQ ID NO: 18:

Lys Lys Lys Lys Lys Lys Lys Lys Lys Lys Lys Lys Lys Lys Lys
1           5                10             15

Lys Lys Lys Lys Lys Val Thr Lys
       20

(2) INFORMATION FOR SEQ ID NO: 19:

(i) SEQUENCE CHARACTERISTICS:
        (A) LENGTH:                   25 amino acids
        (B) TYPE:                     amino acid
        (C) STRANDEDNESS:        single
        (D) TOPOLOGY:             linear (ii) MOLECULE TYPE:         peptide (xi) SEQUENCE DESCRIPTION: SEQ ID NO: 19:

Lys Lys Lys Lys Lys Lys Lys Lys Lys Lys Lys Lys Lys Lys Lys
1           5                10             15

Lys Lys Lys Lys Lys Lys Val Thr Lys
       20           25

(2) INFORMATION FOR SEQ ID NO: 20:

(i) SEQUENCE CHARACTERISTICS:
        (A) LENGTH:                   26 amino acids
        (B) TYPE:                     amino acid
        (C) STRANDEDNESS:        single
        (D) TOPOLOGY:             linear (ii) MOLECULE TYPE:         peptide (xi) SEQUENCE DESCRIPTION: SEQ ID NO: 20:

Lys Lys Lys Lys Lys Lys Lys Lys Lys Lys Lys Lys Lys Lys Lys
1           5                10             15

Lys Lys Lys Lys Lys Lys Lys Val Thr Lys
       20           25

(2) INFORMATION FOR SEQ ID NO: 21:

(i) SEQUENCE CHARACTERISTICS:

```
        (A) LENGTH:              27 amino acids
        (B) TYPE:                amino acid
        (C) STRANDEDNESS:        single
        (D) TOPOLOGY:            linear (ii) MOLECULE TYPE:          peptide (xi) SEQUENCE DESCRIPTION: SEQ ID NO: 21:

Lys Lys Lys Lys Lys Lys Lys Lys Lys Lys Lys Lys Lys Lys Lys Lys
1               5                   10                  15
Lys Lys Lys Lys Lys Lys Lys Lys Val Thr Lys
            20                  25

(2) INFORMATION FOR SEQ ID NO: 22:

(i) SEQUENCE CHARACTERISTICS:
        (A) LENGTH:              28 amino acids
        (B) TYPE:                amino acid
        (C) STRANDEDNESS:        single
        (D) TOPOLOGY:            linear (ii) MOLECULE TYPE:          peptide (xi) SEQUENCE DESCRIPTION: SEQ ID NO: 22:

Lys Lys Lys Lys Lys Lys Lys Lys Lys Lys Lys Lys Lys Lys Lys Lys
1               5                   10                  15
Lys Lys Lys Lys Lys Lys Lys Lys Lys Val Thr Lys
            20                  25

(2) INFORMATION FOR SEQ ID NO: 23:

(i) SEQUENCE CHARACTERISTICS:
        (A) LENGTH:              29 amino acids
        (B) TYPE:                amino acid
        (C) STRANDEDNESS:        single
        (D) TOPOLOGY:            linear (ii) MOLECULE TYPE:          peptide (xi) SEQUENCE DESCRIPTION: SEQ ID NO: 23:

Lys Lys Lys Lys Lys Lys Lys Lys Lys Lys Lys Lys Lys Lys Lys Lys
1               5                   10                  15
Lys Lys Lys Lys Lys Lys Lys Lys Lys Lys Val Thr Lys
            20                  25

(2) INFORMATION FOR SEQ ID NO: 24:

(i) SEQUENCE CHARACTERISTICS:
        (A) LENGTH:              30 amino acids
        (B) TYPE:                amino acid
        (C) STRANDEDNESS:        single
        (D) TOPOLOGY:            linear (ii) MOLECULE TYPE:          peptide (xi) SEQUENCE DESCRIPTION: SEQ ID NO: 24:

Lys Lys Lys Lys Lys Lys Lys Lys Lys Lys Lys Lys Lys Lys Lys Lys
1               5                   10                  15
Lys Lys Lys Lys Lys Lys Lys Lys Lys Lys Lys Val Thr Lys
            20                  25                  30

(2) INFORMATION FOR SEQ ID NO: 25:

(i) SEQUENCE CHARACTERISTICS:
        (A) LENGTH:              31 amino acids
        (B) TYPE:                amino acid
        (C) STRANDEDNESS:        single
```

-continued

```
            (D) TOPOLOGY:           linear (ii) MOLECULE TYPE:         peptide (xi) SEQUENCE DESCRIPTION: SEQ ID NO: 25:

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Val Thr Lys
            20                  25                  30

(2) INFORMATION FOR SEQ ID NO: 26:

(i) SEQUENCE CHARACTERISTICS:
            (A) LENGTH:             32 amino acids
            (B) TYPE:               amino acid
            (C) STRANDEDNESS:       single
            (D) TOPOLOGY:           linear (ii) MOLECULE TYPE:         peptide (xi) SEQUENCE DESCRIPTION: SEQ ID NO: 26:

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Val Thr Lys
            20                  25                  30

(2) INFORMATION FOR SEQ ID NO: 27:

(i) SEQUENCE CHARACTERISTICS:
            (A) LENGTH:             33 amino acids
            (B) TYPE:               amino acid
            (C) STRANDEDNESS:       single
            (D) TOPOLOGY:           linear (ii) MOLECULE TYPE:         peptide (xi) SEQUENCE DESCRIPTION: SEQ ID NO: 27:

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Val Thr
            20                  25                  30

Lys (2) INFORMATION FOR SEQ ID NO: 28:

(i) SEQUENCE CHARACTERISTICS:
            (A) LENGTH:             34 amino acids
            (B) TYPE:               amino acid
            (C) STRANDEDNESS:       single
            (D) TOPOLOGY:           linear (ii) MOLECULE TYPE:         peptide (xi) SEQUENCE DESCRIPTION: SEQ ID NO: 28:

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Val
            20                  25                  30

Thr Lys (2) INFORMATION FOR SEQ ID NO: 29:

(i) SEQUENCE CHARACTERISTICS:
            (A) LENGTH:             35 amino acids
            (B) TYPE:               amino acid
```

```
            (C) STRANDEDNESS:       single
            (D) TOPOLOGY:           linear (ii) MOLECULE TYPE:             peptide (xi) SEQUENCE DESCRIPTION: SEQ ID NO: 29:

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys Lys Lys
            20                  25                  30

Val Thr Lys
        35

(2) INFORMATION FOR SEQ ID NO: 30:

(i) SEQUENCE CHARACTERISTICS:
            (A) LENGTH:             36 amino acids
            (B) TYPE:               amino acid
            (C) STRANDEDNESS:       single
            (D) TOPOLOGY:           linear (ii) MOLECULE TYPE:             peptide (xi) SEQUENCE DESCRIPTION: SEQ ID NO: 30:

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys Lys Lys
            20                  25                  30

Lys Val Thr Lys
        35

(2) INFORMATION FOR SEQ ID NO: 31:

(i) SEQUENCE CHARACTERISTICS:
            (A) LENGTH:             37 amino acids
            (B) TYPE:               amino acid
            (C) STRANDEDNESS:       single
            (D) TOPOLOGY:           linear (ii) MOLECULE TYPE:             peptide (xi) SEQUENCE DESCRIPTION: SEQ ID NO: 31:

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys Lys Lys
            20                  25                  30

Lys Lys Val Thr Lys
        35

(2) INFORMATION FOR SEQ ID NO: 32:

(i) SEQUENCE CHARACTERISTICS:
            (A) LENGTH:             38 amino acids
            (B) TYPE:               amino acid
            (C) STRANDEDNESS:       single
            (D) TOPOLOGY:           linear (ii) MOLECULE TYPE:             peptide (xi) SEQUENCE DESCRIPTION: SEQ ID NO: 32:

Lys Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys Lys Lys
            20                  25                  30
```

```
Lys Lys Lys Val Thr Lys
        35

(2) INFORMATION FOR SEQ ID NO: 33:

(i) SEQUENCE CHARACTERISTICS:
        (A) LENGTH:             39 amino acids
        (B) TYPE:               amino acid
        (C) STRANDEDNESS:       single
        (D) TOPOLOGY:           linear (ii) MOLECULE TYPE:         peptide (xi) SEQUENCE DESCRIPTION: SEQ ID NO: 33:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Val Thr Lys
        35

(2) INFORMATION FOR SEQ ID NO: 34:

(i) SEQUENCE CHARACTERISTICS:
        (A) LENGTH:             40 amino acids
        (B) TYPE:               amino acid
        (C) STRANDEDNESS:       single
        (D) TOPOLOGY:           linear (ii) MOLECULE TYPE:         peptide (xi) SEQUENCE DESCRIPTION: SEQ ID NO: 34:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Val Thr Lys
        35              40

(2) INFORMATION FOR SEQ ID NO: 35:

(i) SEQUENCE CHARACTERISTICS:
        (A) LENGTH:             41 amino acids
        (B) TYPE:               amino acid
        (C) STRANDEDNESS:       single
        (D) TOPOLOGY:           linear (ii) MOLECULE TYPE:         peptide (xi) SEQUENCE DESCRIPTION: SEQ ID NO: 35:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Val Thr Lys
        35              40

(2) INFORMATION FOR SEQ ID NO: 36:

(i) SEQUENCE CHARACTERISTICS:
        (A) LENGTH:             42 amino acids
        (B) TYPE:               amino acid
        (C) STRANDEDNESS:       single
        (D) TOPOLOGY:           linear (ii) MOLECULE TYPE:         peptide
```

(xi) SEQUENCE DESCRIPTION: SEQ ID NO: 36:

Lys Lys Lys Lys Lys Lys Lys Lys Lys Lys Lys Lys Lys Lys Lys Lys
  1               5                  10                  15

Lys Lys Lys Lys Lys Lys Lys Lys Lys Lys Lys Lys Lys Lys Lys Lys
                 20                  25                  30

Lys Lys Lys Lys Lys Lys Lys Val Thr Lys
         35                  40

(2) INFORMATION FOR SEQ ID NO: 37:

(i) SEQUENCE CHARACTERISTICS:
        (A) LENGTH:            43 amino acids
        (B) TYPE:              amino acid
        (C) STRANDEDNESS:      single
        (D) TOPOLOGY:          linear (ii) MOLECULE TYPE:        peptide (xi) SEQUENCE DESCRIPTION: SEQ ID NO: 37:

Lys Lys Lys Lys Lys Lys Lys Lys Lys Lys Lys Lys Lys Lys Lys Lys
  1               5                  10                  15

Lys Lys Lys Lys Lys Lys Lys Lys Lys Lys Lys Lys Lys Lys Lys Lys
                 20                  25                  30

Lys Lys Lys Lys Lys Lys Lys Val Thr Lys
         35                  40

(2) INFORMATION FOR SEQ ID NO: 38:

(i) SEQUENCE CHARACTERISTICS:
        (A) LENGTH:            44 amino acids
        (B) TYPE:              amino acid
        (C) STRANDEDNESS:      single
        (D) TOPOLOGY:          linear (ii) MOLECULE TYPE:        peptide (xi) SEQUENCE DESCRIPTION: SEQ ID NO: 38:

Lys Lys Lys Lys Lys Lys Lys Lys Lys Lys Lys Lys Lys Lys Lys Lys
  1               5                  10                  15

Lys Lys Lys Lys Lys Lys Lys Lys Lys Lys Lys Lys Lys Lys Lys Lys
                 20                  25                  30

Lys Lys Lys Lys Lys Lys Lys Lys Val Thr Lys
         35                  40

(2) INFORMATION FOR SEQ ID NO: 39:

(i) SEQUENCE CHARACTERISTICS:
        (A) LENGTH:            7 amino acids
        (B) TYPE:              amino acid
        (C) STRANDEDNESS:      single
        (D) TOPOLOGY:          linear (ii) MOLECULE TYPE:        peptide (ix) FEATURE:
        (D) OTHER INFORMATION: "Xaa" stands for any naturally
            occurring amino acid and
            analogues thereof.

(xi) SEQUENCE DESCRIPTION: SEQ ID NO: 39:

Lys Lys Lys Lys Lys Xaa Lys
  1               5

(2) INFORMATION FOR SEQ ID NO: 40:

(i) SEQUENCE CHARACTERISTICS:
           (A) LENGTH:              8 amino acids
           (B) TYPE:                amino acid
           (C) STRANDEDNESS:        single
           (D) TOPOLOGY:            linear (ii) MOLECULE TYPE:           peptide (ix) FEATURE:
           (D) OTHER INFORMATION:   "Xaa" stands for any naturally
               occurring amino acid and
               analogues thereof.

(xi) SEQUENCE DESCRIPTION: SEQ ID NO: 40:

Lys Lys Lys Lys Lys Lys Xaa Lys
1               5

(2) INFORMATION FOR SEQ ID NO: 41:

(i) SEQUENCE CHARACTERISTICS:
           (A) LENGTH:              9 amino acids
           (B) TYPE:                amino acid
           (C) STRANDEDNESS:        single
           (D) TOPOLOGY:            linear (ii) MOLECULE TYPE:           peptide (ix) FEATURE:
           (D) OTHER INFORMATION:   "Xaa" stands for any naturally
               occurring amino acid and
               analogues thereof.

(xi) SEQUENCE DESCRIPTION: SEQ ID NO: 41:

Lys Lys Lys Lys Lys Lys Lys Xaa Lys
1               5

(2) INFORMATION FOR SEQ ID NO: 42:

(i) SEQUENCE CHARACTERISTICS:
           (A) LENGTH:              10 amino acids
           (B) TYPE:                amino acid
           (C) STRANDEDNESS:        single
           (D) TOPOLOGY:            linear (ii) MOLECULE TYPE:           peptide (ix) FEATURE:
           (D) OTHER INFORMATION:   "Xaa" stands for any naturally
               occurring amino acid and
               analogues thereof.

(xi) SEQUENCE DESCRIPTION: SEQ ID NO: 42:

Lys Lys Lys Lys Lys Lys Lys Lys Xaa Lys
1               5                   10

(2) INFORMATION FOR SEQ ID NO: 43:

(i) SEQUENCE CHARACTERISTICS:
           (A) LENGTH:              11 amino acids
           (B) TYPE:                amino acid
           (C) STRANDEDNESS:        single
           (D) TOPOLOGY:            linear (ii) MOLECULE TYPE:           peptide (ix) FEATURE:
           (D) OTHER INFORMATION:   "Xaa" stands for any naturally
               occurring amino acid and
               analogues thereof.

(xi) SEQUENCE DESCRIPTION: SEQ ID NO: 43:

Lys Lys Lys Lys Lys Lys Lys Lys Lys Xaa Lys
1               5                   10

(2) INFORMATION FOR SEQ ID NO: 44:

(i) SEQUENCE CHARACTERISTICS:
        (A) LENGTH:            12 amino acids
        (B) TYPE:              amino acid
        (C) STRANDEDNESS:      single
        (D) TOPOLOGY:          linear (ii) MOLECULE TYPE:            peptide (ix) FEATURE:
        (D) OTHER INFORMATION:   "Xaa" stands for any naturally
            occurring amino acid and
            analogues thereof.

(xi) SEQUENCE DESCRIPTION: SEQ ID NO: 44:

Lys Lys Lys Lys Lys Lys Lys Lys Lys Lys Xaa Lys
1               5                   10

(2) INFORMATION FOR SEQ ID NO: 45:

(i) SEQUENCE CHARACTERISTICS:
        (A) LENGTH:            13 amino acids
        (B) TYPE:              amino acid
        (C) STRANDEDNESS:      single
        (D) TOPOLOGY:          linear (ii) MOLECULE TYPE:            peptide (ix) FEATURE:
        (D) OTHER INFORMATION:   "Xaa" stands for any naturally
            occurring amino acid and
            analogues thereof.

(xi) SEQUENCE DESCRIPTION: SEQ ID NO: 45:

Lys Lys Lys Lys Lys Lys Lys Lys Lys Lys Lys Xaa Lys
1               5                   10

(2) INFORMATION FOR SEQ ID NO: 46:

(i) SEQUENCE CHARACTERISTICS:
        (A) LENGTH:            14 amino acids
        (B) TYPE:              amino acid
        (C) STRANDEDNESS:      single
        (D) TOPOLOGY:          linear (ii) MOLECULE TYPE:            peptide (ix) FEATURE:
        (D) OTHER INFORMATION:   "Xaa" stands for any naturally
            occurring amino acid and
            analogues thereof.

(xi) SEQUENCE DESCRIPTION: SEQ ID NO: 46:

Lys Lys Lys Lys Lys Lys Lys Lys Lys Lys Lys Lys Xaa Lys
1               5                   10

(2) INFORMATION FOR SEQ ID NO: 47:

(i) SEQUENCE CHARACTERISTICS:
        (A) LENGTH:            15 amino acids
        (B) TYPE:              amino acid
        (C) STRANDEDNESS:      single
        (D) TOPOLOGY:          linear (ii) MOLECULE TYPE:            peptide (ix) FEATURE:
        (D) OTHER INFORMATION:   "Xaa" stands for any naturally

```
                  occurring amino acid and
                  analogues thereof.

(xi) SEQUENCE DESCRIPTION: SEQ ID NO:  47:

Lys Lys Lys Lys Lys Lys Lys Lys Lys Lys Lys Lys Lys Lys Xaa Lys
1               5                   10                  15

(2) INFORMATION FOR SEQ ID NO: 48:

(i) SEQUENCE CHARACTERISTICS:
          (A) LENGTH:              16 amino acids
          (B) TYPE:                amino acid
          (C) STRANDEDNESS:        single
          (D) TOPOLOGY:            linear (ii) MOLECULE TYPE:            peptide (ix) FEATURE:
          (D) OTHER INFORMATION:   "Xaa" stands for any naturally
                  occurring amino acid and
                  analogues thereof.

(xi) SEQUENCE DESCRIPTION: SEQ ID NO:  48:

Lys Lys Lys Lys Lys Lys Lys Lys Lys Lys Lys Lys Lys Lys Xaa Lys
1               5                   10                  15

(2) INFORMATION FOR SEQ ID NO: 49:

(i) SEQUENCE CHARACTERISTICS:
          (A) LENGTH:              17 amino acids
          (B) TYPE:                amino acid
          (C) STRANDEDNESS:        single
          (D) TOPOLOGY:            linear (ii) MOLECULE TYPE:            peptide (ix) FEATURE:
          (D) OTHER INFORMATION:   "Xaa" stands for any naturally
                  occurring amino acid and
                  analogues thereof.

(xi) SEQUENCE DESCRIPTION: SEQ ID NO:  49:

Lys Lys Lys Lys Lys Lys Lys Lys Lys Lys Lys Lys Lys Lys Lys Xaa
1               5                   10                  15

Lys (2) INFORMATION FOR SEQ ID NO: 50:

(i) SEQUENCE CHARACTERISTICS:
          (A) LENGTH:              18 amino acids
          (B) TYPE:                amino acid
          (C) STRANDEDNESS:        single
          (D) TOPOLOGY:            linear (ii) MOLECULE TYPE:            peptide (ix) FEATURE:
          (D) OTHER INFORMATION:   "Xaa" stands for any naturally
                  occurring amino acid and
                  analogues thereof.

(xi) SEQUENCE DESCRIPTION: SEQ ID NO:  50:

Lys Lys Lys Lys Lys Lys Lys Lys Lys Lys Lys Lys Lys Lys Lys Lys
1               5                   10                  15

Xaa Lys (2) INFORMATION FOR SEQ ID NO: 51:

(i) SEQUENCE CHARACTERISTICS:
```

```
            (A) LENGTH:              19 amino acids
            (B) TYPE:                amino acid
            (C) STRANDEDNESS:        single
            (D) TOPOLOGY:            linear (ii) MOLECULE TYPE:            peptide (ix) FEATURE:
            (D) OTHER INFORMATION:   "Xaa" stands for any naturally
                  occurring amino acid and
                  analogues thereof.

(xi) SEQUENCE DESCRIPTION: SEQ ID NO: 51:

Lys Lys Lys Lys Lys Lys Lys Lys Lys Lys Lys Lys Lys Lys Lys
 1               5                  10                  15

Lys Xaa Lys (2) INFORMATION FOR SEQ ID NO: 52:

(i) SEQUENCE CHARACTERISTICS:
            (A) LENGTH:              20 amino acids
            (B) TYPE:                amino acid
            (C) STRANDEDNESS:        single
            (D) TOPOLOGY:            linear (ii) MOLECULE TYPE:            peptide (ix) FEATURE:
            (D) OTHER INFORMATION:   "Xaa" stands for any naturally
                  occurring amino acid and
                  analogues thereof.

(xi) SEQUENCE DESCRIPTION: SEQ ID NO: 52:

Lys Lys Lys Lys Lys Lys Lys Lys Lys Lys Lys Lys Lys Lys Lys
 1               5                  10                  15

Lys Lys Xaa Lys
            20

(2) INFORMATION FOR SEQ ID NO: 53:

(i) SEQUENCE CHARACTERISTICS:
            (A) LENGTH:              21 amino acids
            (B) TYPE:                amino acid
            (C) STRANDEDNESS:        single
            (D) TOPOLOGY:            linear (ii) MOLECULE TYPE:            peptide (ix) FEATURE:
            (D) OTHER INFORMATION:   "Xaa" stands for any naturally
                  occurring amino acid and
                  analogues thereof.

(xi) SEQUENCE DESCRIPTION: SEQ ID NO: 53:

Lys Lys Lys Lys Lys Lys Lys Lys Lys Lys Lys Lys Lys Lys Lys
 1               5                  10                  15

Lys Lys Lys Xaa Lys
            20

(2) INFORMATION FOR SEQ ID NO: 54:

(i) SEQUENCE CHARACTERISTICS:
            (A) LENGTH:              22 amino acids
            (B) TYPE:                amino acid
            (C) STRANDEDNESS:        single
            (D) TOPOLOGY:            linear (ii) MOLECULE TYPE:            peptide (ix) FEATURE:
```

```
            (D) OTHER INFORMATION:   "Xaa" stands for any naturally
                occurring amino acid and
                analogues thereof.

(xi) SEQUENCE DESCRIPTION: SEQ ID NO:  54:

Lys Lys Lys Lys Lys Lys Lys Lys Lys Lys Lys Lys Lys Lys Lys Lys
  1               5                  10                  15

Lys Lys Lys Lys Xaa Lys
            20

(2) INFORMATION FOR SEQ ID NO:  55:

(i) SEQUENCE CHARACTERISTICS:
        (A) LENGTH:              23 amino acids
        (B) TYPE:                amino acid
        (C) STRANDEDNESS:        single
        (D) TOPOLOGY:            linear (ii) MOLECULE TYPE:          peptide (ix) FEATURE:
        (D) OTHER INFORMATION:   "Xaa" stands for any naturally
            occurring amino acid and
            analogues thereof.

(xi) SEQUENCE DESCRIPTION: SEQ ID NO:  55:

Lys Lys Lys Lys Lys Lys Lys Lys Lys Lys Lys Lys Lys Lys Lys Lys
  1               5                  10                  15

Lys Lys Lys Lys Lys Xaa Lys
            20

(2) INFORMATION FOR SEQ ID NO:  56:

(i) SEQUENCE CHARACTERISTICS:
        (A) LENGTH:              24 amino acids
        (B) TYPE:                amino acid
        (C) STRANDEDNESS:        single
        (D) TOPOLOGY:            linear (ii) MOLECULE TYPE:          peptide (ix) FEATURE:
        (D) OTHER INFORMATION:   "Xaa" stands for any naturally
            occurring amino acid and
            analogues thereof.

(xi) SEQUENCE DESCRIPTION: SEQ ID NO:  56:

Lys Lys Lys Lys Lys Lys Lys Lys Lys Lys Lys Lys Lys Lys Lys Lys
  1               5                  10                  15

Lys Lys Lys Lys Lys Lys Xaa Lys
            20

(2) INFORMATION FOR SEQ ID NO:  57:

(i) SEQUENCE CHARACTERISTICS:
        (A) LENGTH:              25 amino acids
        (B) TYPE:                amino acid
        (C) STRANDEDNESS:        single
        (D) TOPOLOGY:            linear (ii) MOLECULE TYPE:          peptide (ix) FEATURE:
        (D) OTHER INFORMATION:   "Xaa" stands for any naturally
            occurring amino acid and
            analogues thereof.

(xi) SEQUENCE DESCRIPTION: SEQ ID NO:  57:

Lys Lys Lys Lys Lys Lys Lys Lys Lys Lys Lys Lys Lys Lys Lys Lys
```

-continued

```
                1               5                    10                   15
Lys Lys Lys Lys Lys Lys Lys Xaa Lys
                20                   25
```

(2) INFORMATION FOR SEQ ID NO: 58:

(i) SEQUENCE CHARACTERISTICS:
        (A) LENGTH:           26 amino acids
        (B) TYPE:             amino acid
        (C) STRANDEDNESS:     single
        (D) TOPOLOGY:         linear (ii) MOLECULE TYPE:         peptide (ix) FEATURE:
        (D) OTHER INFORMATION:  "Xaa" stands for any naturally
            occurring amino acid and
            analogues thereof.

(xi) SEQUENCE DESCRIPTION: SEQ ID NO: 58:

```
Lys Lys Lys Lys Lys Lys Lys Lys Lys Lys Lys Lys Lys Lys Lys
1               5                    10                   15
Lys Lys Lys Lys Lys Lys Lys Lys Xaa Lys
                20                   25
```

(2) INFORMATION FOR SEQ ID NO: 59:

(i) SEQUENCE CHARACTERISTICS:
        (A) LENGTH:           27 amino acids
        (B) TYPE:             amino acid
        (C) STRANDEDNESS:     single
        (D) TOPOLOGY:         linear (ii) MOLECULE TYPE:         peptide (ix) FEATURE:
        (D) OTHER INFORMATION:  "Xaa" stands for any naturally
            occurring amino acid and
            analogues thereof.

(xi) SEQUENCE DESCRIPTION: SEQ ID NO: 59:

```
Lys Lys Lys Lys Lys Lys Lys Lys Lys Lys Lys Lys Lys Lys Lys
1               5                    10                   15
Lys Lys Lys Lys Lys Lys Lys Lys Lys Xaa Lys
                20                   25
```

(2) INFORMATION FOR SEQ ID NO: 60:

(i) SEQUENCE CHARACTERISTICS:
        (A) LENGTH:           28 amino acids
        (B) TYPE:             amino acid
        (C) STRANDEDNESS:     single
        (D) TOPOLOGY:         linear (ii) MOLECULE TYPE:         peptide (ix) FEATURE:
        (D) OTHER INFORMATION:  "Xaa" stands for any naturally
            occurring amino acid and
            analogues thereof.

(xi) SEQUENCE DESCRIPTION: SEQ ID NO: 60:

```
Lys Lys Lys Lys Lys Lys Lys Lys Lys Lys Lys Lys Lys Lys Lys
1               5                    10                   15
Lys Lys Lys Lys Lys Lys Lys Lys Lys Lys Xaa Lys
                20                   25
```

(2) INFORMATION FOR SEQ ID NO: 61:

(i) SEQUENCE CHARACTERISTICS:
    (A) LENGTH:           29 amino acids
    (B) TYPE:             amino acid
    (C) STRANDEDNESS:    single
    (D) TOPOLOGY:        linear (ii) MOLECULE TYPE:        peptide (ix) FEATURE:
    (D) OTHER INFORMATION:   "Xaa" stands for any naturally
        occurring amino acid and
        analogues thereof.

(xi) SEQUENCE DESCRIPTION: SEQ ID NO: 61:

Lys Lys Lys Lys Lys Lys Lys Lys Lys Lys Lys Lys Lys Lys Lys
1          5                  10              15

Lys Lys Lys Lys Lys Lys Lys Lys Lys Lys Xaa Lys
        20              25

(2) INFORMATION FOR SEQ ID NO: 62:

(i) SEQUENCE CHARACTERISTICS:
        (A) LENGTH:           30 amino acids
        (B) TYPE:             amino acid
        (C) STRANDEDNESS:    single
        (D) TOPOLOGY:        linear (ii) MOLECULE TYPE:        peptide (ix) FEATURE:
        (D) OTHER INFORMATION:   "Xaa" stands for any naturally
            occurring amino acid and
            analogues thereof.

(xi) SEQUENCE DESCRIPTION: SEQ ID NO: 62:

Lys Lys Lys Lys Lys Lys Lys Lys Lys Lys Lys Lys Lys Lys Lys
1          5                  10              15

Lys Lys Lys Lys Lys Lys Lys Lys Lys Lys Lys Xaa Lys
        20              25              30

(2) INFORMATION FOR SEQ ID NO: 63:

(i) SEQUENCE CHARACTERISTICS:
        (A) LENGTH:           31 amino acids
        (B) TYPE:             amino acid
        (C) STRANDEDNESS:    single
        (D) TOPOLOGY:        linear (ii) MOLECULE TYPE:        peptide (ix) FEATURE:
        (D) OTHER INFORMATION:   "Xaa" stands for any naturally
            occurring amino acid and
            analogues thereof.

(xi) SEQUENCE DESCRIPTION: SEQ ID NO: 63:

Lys Lys Lys Lys Lys Lys Lys Lys Lys Lys Lys Lys Lys Lys Lys
1          5                  10              15

Lys Lys Lys Lys Lys Lys Lys Lys Lys Lys Lys Lys Xaa Lys
        20              25              30

(2) INFORMATION FOR SEQ ID NO: 64:

(i) SEQUENCE CHARACTERISTICS:
        (A) LENGTH:           32 amino acids
        (B) TYPE:             amino acid
        (C) STRANDEDNESS:    single
        (D) TOPOLOGY:        linear

```
        (ii) MOLECULE TYPE:           peptide (ix) FEATURE:
             (D) OTHER INFORMATION:   "Xaa" stands for any naturally
                 occurring amino acid and
                 analogues thereof.

(xi) SEQUENCE DESCRIPTION: SEQ ID NO:  64:

Lys Lys Lys Lys Lys Lys Lys Lys Lys Lys Lys Lys Lys Lys Lys Lys
  1               5                  10                  15

Lys Lys Lys Lys Lys Lys Lys Lys Lys Lys Lys Lys Lys Xaa Lys
             20                  25                  30

(2) INFORMATION FOR SEQ ID NO:  65:

(i) SEQUENCE CHARACTERISTICS:
             (A) LENGTH:              33 amino acids
             (B) TYPE:                amino acid
             (C) STRANDEDNESS:        single
             (D) TOPOLOGY:            linear (ii) MOLECULE TYPE:           peptide (ix) FEATURE:
             (D) OTHER INFORMATION:   "Xaa" stands for any naturally
                 occurring amino acid and
                 analogues thereof.

(xi) SEQUENCE DESCRIPTION: SEQ ID NO:  65:

Lys Lys Lys Lys Lys Lys Lys Lys Lys Lys Lys Lys Lys Lys Lys Lys
  1               5                  10                  15

Lys Lys Lys Lys Lys Lys Lys Lys Lys Lys Lys Lys Lys Lys Xaa
             20                  25                  30

Lys (2) INFORMATION FOR SEQ ID NO:  66:

(i) SEQUENCE CHARACTERISTICS:
             (A) LENGTH:              34 amino acids
             (B) TYPE:                amino acid
             (C) STRANDEDNESS:        single
             (D) TOPOLOGY:            linear (ii) MOLECULE TYPE:           peptide (ix) FEATURE:
             (D) OTHER INFORMATION:   "Xaa" stands for any naturally
                 occurring amino acid and
                 analogues thereof.

(xi) SEQUENCE DESCRIPTION: SEQ ID NO:  66:

Lys Lys Lys Lys Lys Lys Lys Lys Lys Lys Lys Lys Lys Lys Lys Lys
  1               5                  10                  15

Lys Lys Lys Lys Lys Lys Lys Lys Lys Lys Lys Lys Lys Lys Lys Lys
             20                  25                  30

Xaa Lys (2) INFORMATION FOR SEQ ID NO:  67:

(i) SEQUENCE CHARACTERISTICS:
             (A) LENGTH:              35 amino acids
             (B) TYPE:                amino acid
             (C) STRANDEDNESS:        single
             (D) TOPOLOGY:            linear (ii) MOLECULE TYPE:           peptide (ix) FEATURE:
```

(D) OTHER INFORMATION:   "Xaa" stands for any naturally
            occurring amino acid and
            analogues thereof.

(xi) SEQUENCE DESCRIPTION: SEQ ID NO:  67:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
        20                  25                  30

Lys Xaa Lys
        35

(2) INFORMATION FOR SEQ ID NO:  68:

(i) SEQUENCE CHARACTERISTICS:
        (A) LENGTH:             36 amino acids
        (B) TYPE:               amino acid
        (C) STRANDEDNESS:       single
        (D) TOPOLOGY:           linear (ii) MOLECULE TYPE:         peptide (ix) FEATURE:
        (D) OTHER INFORMATION:   "Xaa" stands for any naturally
            occurring amino acid and
            analogues thereof.

(xi) SEQUENCE DESCRIPTION: SEQ ID NO:  68:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
        20                  25                  30

Lys Lys Xaa Lys
        35

(2) INFORMATION FOR SEQ ID NO:  69:

(i) SEQUENCE CHARACTERISTICS:
        (A) LENGTH:             37 amino acids
        (B) TYPE:               amino acid
        (C) STRANDEDNESS:       single
        (D) TOPOLOGY:           linear (ii) MOLECULE TYPE:         peptide (ix) FEATURE:
        (D) OTHER INFORMATION:   "Xaa" stands for any naturally
            occurring amino acid and
            analogues thereof.

(xi) SEQUENCE DESCRIPTION: SEQ ID NO:  69:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
        20                  25                  30

Lys Lys Lys Xaa Lys
        35

(2) INFORMATION FOR SEQ ID NO:  70:

(i) SEQUENCE CHARACTERISTICS:
        (A) LENGTH:             38 amino acids
        (B) TYPE:               amino acid
        (C) STRANDEDNESS:       single
        (D) TOPOLOGY:           linear (ii) MOLECULE TYPE:         peptide

```
        (ix) FEATURE:
             (D) OTHER INFORMATION:    "Xaa" stands for any naturally
                 occurring amino acid and
                 analogues thereof.

(xi) SEQUENCE DESCRIPTION: SEQ ID NO:  70:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
        20                  25                  30

Lys Lys Lys Lys Xaa Lys
        35

(2) INFORMATION FOR SEQ ID NO:  71:

(i) SEQUENCE CHARACTERISTICS:
             (A) LENGTH:            39 amino acids
             (B) TYPE:              amino acid
             (C) STRANDEDNESS:      single
             (D) TOPOLOGY:          linear (ii) MOLECULE TYPE:         peptide (ix) FEATURE:
             (D) OTHER INFORMATION:    "Xaa" stands for any naturally
                 occurring amino acid and
                 analogues thereof.

(xi) SEQUENCE DESCRIPTION: SEQ ID NO:  71:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
        20                  25                  30

Lys Lys Lys Lys Lys Xaa Lys
        35

(2) INFORMATION FOR SEQ ID NO:  72:

(i) SEQUENCE CHARACTERISTICS:
             (A) LENGTH:            40 amino acids
             (B) TYPE:              amino acid
             (C) STRANDEDNESS:      single
             (D) TOPOLOGY:          linear (ii) MOLECULE TYPE:         peptide (ix) FEATURE:
             (D) OTHER INFORMATION:    "Xaa" stands for any naturally
                 occurring amino acid and
                 analogues thereof.

(xi) SEQUENCE DESCRIPTION: SEQ ID NO:  72:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
        20                  25                  30

Lys Lys Lys Lys Lys Lys Xaa Lys
        35                  40

(2) INFORMATION FOR SEQ ID NO:  73:

(i) SEQUENCE CHARACTERISTICS:
             (A) LENGTH:            41 amino acids
             (B) TYPE:              amino acid
             (C) STRANDEDNESS:      single
             (D) TOPOLOGY:          linear
```

(ii) MOLECULE TYPE:             peptide (ix) FEATURE:
             (D) OTHER INFORMATION:   "Xaa" stands for any naturally
                 occurring amino acid and
                 analogues thereof.

(xi) SEQUENCE DESCRIPTION: SEQ ID NO: 73:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Xaa Lys
        35                  40

(2) INFORMATION FOR SEQ ID NO: 74:

(i) SEQUENCE CHARACTERISTICS:
             (A) LENGTH:               42 amino acids
             (B) TYPE:                 amino acid
             (C) STRANDEDNESS:         single
             (D) TOPOLOGY:             linear (ii) MOLECULE TYPE:             peptide (ix) FEATURE:
             (D) OTHER INFORMATION:   "Xaa" stands for any naturally
                 occurring amino acid and
                 analogues thereof.

(xi) SEQUENCE DESCRIPTION: SEQ ID NO: 74:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Xaa Lys
        35                  40

(2) INFORMATION FOR SEQ ID NO: 75:

(i) SEQUENCE CHARACTERISTICS:
             (A) LENGTH:               43 amino acids
             (B) TYPE:                 amino acid
             (C) STRANDEDNESS:         single
             (D) TOPOLOGY:             linear (ii) MOLECULE TYPE:             peptide (ix) FEATURE:
             (D) OTHER INFORMATION:   "Xaa" stands for any naturally
                 occurring amino acid and
                 analogues thereof.

(xi) SEQUENCE DESCRIPTION: SEQ ID NO: 75:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Lys Xaa Lys
        35                  40

(2) INFORMATION FOR SEQ ID NO: 76:

(i) SEQUENCE CHARACTERISTICS:
             (A) LENGTH:               41 amino acids
             (B) TYPE:                 amino acid

```
            (C) STRANDEDNESS:          single
            (D) TOPOLOGY:              linear (ii) MOLECULE TYPE:              peptide (xi) SEQUENCE DESCRIPTION: SEQ ID NO: 76:

Ser Thr Glu Glu Leu Arg Val Arg Leu Ala Ser His Leu Arg Lys Leu
1               5                   10                  15

Arg Lys Arg Leu Leu Arg Asp Ala Asp Asp Leu Gln Lys Arg Leu Ala
            20                  25                  30

Val Tyr Gln Ala Gly Ala Arg Glu Gly
        35                  40

(2) INFORMATION FOR SEQ ID NO: 77:

(i) SEQUENCE CHARACTERISTICS:
            (A) LENGTH:                16 amino acids
            (B) TYPE:                  amino acid
            (C) STRANDEDNESS:          single
            (D) TOPOLOGY:              linear (ii) MOLECULE TYPE:              peptide (xi) SEQUENCE DESCRIPTION: SEQ ID NO: 77:

Lys Lys Gln Leu Lys Lys Gln Leu Lys Lys Gln Leu Lys Gln Trp Lys
1               5                   10                  15

(2) INFORMATION FOR SEQ ID NO: 78:

(i) SEQUENCE CHARACTERISTICS:
            (A) LENGTH:                17 amino acids
            (B) TYPE:                  amino acid
            (C) STRANDEDNESS:          single
            (D) TOPOLOGY:              linear (ii) MOLECULE TYPE:              peptide (xi) SEQUENCE DESCRIPTION: SEQ ID NO: 78:

Lys Lys Ser Pro Lys Lys Ser Pro Lys Lys Ser Pro Lys Lys Ser Trp
1               5                   10                  15

Lys (2) INFORMATION FOR SEQ ID NO: 79:

(i) SEQUENCE CHARACTERISTICS:
            (A) LENGTH:                11 amino acids
            (B) TYPE:                  amino acid
            (C) STRANDEDNESS:          single
            (D) TOPOLOGY:              linear (ii) MOLECULE TYPE:              peptide (xi) SEQUENCE DESCRIPTION: SEQ ID NO: 79:

Lys Arg Arg Arg Arg Arg Arg Arg Trp Arg
1               5                   10

(2) INFORMATION FOR SEQ ID NO: 80:

(i) SEQUENCE CHARACTERISTICS:
            (A) LENGTH:                14 amino acids
            (B) TYPE:                  amino acid
            (C) STRANDEDNESS:          single
            (D) TOPOLOGY:              linear (ii) MOLECULE TYPE:              peptide (xi) SEQUENCE DESCRIPTION: SEQ ID NO: 80:
```

```
Lys Leu Ser Lys Leu Glu Lys Lys Trp Ser Lys Leu Glu Lys
 1               5                   10
```

(2) INFORMATION FOR SEQ ID NO: 81:

(i) SEQUENCE CHARACTERISTICS:
        (A) LENGTH:             21 amino acids
        (B) TYPE:               amino acid
        (C) STRANDEDNESS:     single
        (D) TOPOLOGY:          linear (ii) MOLECULE TYPE:        peptide (xi) SEQUENCE DESCRIPTION: SEQ ID NO: 81:

```
Lys Leu Ser Lys Leu Glu Lys Lys Leu Ser Lys Leu Glu Lys Lys Trp
 1               5                   10                  15
Ser Lys Leu Glu Lys
            20
```

(2) INFORMATION FOR SEQ ID NO: 82:

(i) SEQUENCE CHARACTERISTICS:
        (A) LENGTH:             16 amino acids
        (B) TYPE:               amino acid
        (C) STRANDEDNESS:     single
        (D) TOPOLOGY:          linear (ii) MOLECULE TYPE:        peptide (xi) SEQUENCE DESCRIPTION: SEQ ID NO: 82:

```
Lys Ser Leu Lys Lys Ser Leu Lys Lys Ser Leu Lys Lys Ser Trp Lys
 1               5                   10                  15
```

(2) INFORMATION FOR SEQ ID NO: 83:

(i) SEQUENCE CHARACTERISTICS:
        (A) LENGTH:             24 amino acids
        (B) TYPE:               amino acid
        (C) STRANDEDNESS:     single
        (D) TOPOLOGY:          linear (ii) MOLECULE TYPE:        peptide (xi) SEQUENCE DESCRIPTION: SEQ ID NO: 83:

```
Lys Ser Thr Pro Pro Lys Lys Arg Lys Val Glu Asp Pro Lys Asp
 1               5                   10                  15
Phe Pro Ser Glu Leu Leu Ser Ala
            20
```

(2) INFORMATION FOR SEQ ID NO: 84:

(i) SEQUENCE CHARACTERISTICS:
        (A) LENGTH:             16 amino acids
        (B) TYPE:               amino acid
        (C) STRANDEDNESS:     single
        (D) TOPOLOGY:          linear (ii) MOLECULE TYPE:        peptide (xi) SEQUENCE DESCRIPTION: SEQ ID NO: 84:

```
Lys Ala Lys Lys Lys Lys Asn Lys Ser Ser Lys Lys Lys Lys Trp
 1               5                   10                  15
Lys
```

(2) INFORMATION FOR SEQ ID NO: 85:

(i) SEQUENCE CHARACTERISTICS:

```
                (A) LENGTH:              22 amino acids
                (B) TYPE:                amino acid
                (C) STRANDEDNESS:        single
                (D) TOPOLOGY:            linear (ii) MOLECULE TYPE:              peptide (xi) SEQUENCE DESCRIPTION: SEQ ID NO: 85:

Lys Ile Arg Arg Arg Gly Lys Asn Lys Val Ala Ala Arg Thr Cys Arg
1               5                   10                  15

Gln Arg Arg Thr Asp Arg
            20

(2) INFORMATION FOR SEQ ID NO: 86:

(i) SEQUENCE CHARACTERISTICS:
                (A) LENGTH:              15 amino acids
                (B) TYPE:                amino acid
                (C) STRANDEDNESS:        single
                (D) TOPOLOGY:            linear (ii) MOLECULE TYPE:              peptide (ix) FEATURE:
                (D) OTHER INFORMATION:   "Xaa" stands for Alanine
                    or Serine.

(xi) SEQUENCE DESCRIPTION: SEQ ID NO: 86:

Lys Xaa Lys Lys Xaa Lys Lys Lys Xaa Lys Lys Xaa Lys Trp Lys
1               5                   10                  15

(2) INFORMATION FOR SEQ ID NO: 87:

(i) SEQUENCE CHARACTERISTICS:
                (A) LENGTH:              22 amino acids
                (B) TYPE:                amino acid
                (C) STRANDEDNESS:        single
                (D) TOPOLOGY:            linear (ii) MOLECULE TYPE:              peptide (xi) SEQUENCE DESCRIPTION: SEQ ID NO: 87:

Lys Ile Arg Arg Arg Gly Lys Asn Lys Ala Ala Ala Arg Thr Cys Arg
1               5                   10                  15

Glu Arg Arg Arg Ser Lys
            20

(2) INFORMATION FOR SEQ ID NO: 88:

(i) SEQUENCE CHARACTERISTICS:
                (A) LENGTH:              22 amino acids
                (B) TYPE:                amino acid
                (C) STRANDEDNESS:        single
                (D) TOPOLOGY:            linear (ii) MOLECULE TYPE:              peptide (xi) SEQUENCE DESCRIPTION: SEQ ID NO: 88:

Lys Ile Arg Arg Arg Gly Lys Asn Lys Val Ala Ala Gln Asn Cys Arg
1               5                   10                  15

Lys Arg Lys Leu Asp Gln
            20

(2) INFORMATION FOR SEQ ID NO: 89:

(i) SEQUENCE CHARACTERISTICS:
                (A) LENGTH:              22 amino acids
                (B) TYPE:                amino acid
```

(C) STRANDEDNESS:         single
            (D) TOPOLOGY:             linear (ii) MOLECULE TYPE:             peptide (xi) SEQUENCE DESCRIPTION: SEQ ID NO: 89:

Lys Ile Arg Arg Arg Gly Lys Asn Lys Val Ala Ala Gln Asn Cys Arg
1               5                   10                  15

Lys Arg Lys Leu Glu Thr
            20

(2) INFORMATION FOR SEQ ID NO: 90:

(i) SEQUENCE CHARACTERISTICS:
            (A) LENGTH:               24 amino acids
            (B) TYPE:                 amino acid
            (C) STRANDEDNESS:         single
            (D) TOPOLOGY:             linear (ii) MOLECULE TYPE:             peptide (xi) SEQUENCE DESCRIPTION: SEQ ID NO: 90:

Lys Arg Arg Ile Arg Arg Glu Lys Asn Lys Met Ala Ala Ala Lys Cys
1               5                   10                  15

Arg Asn Arg Arg Arg Glu Leu Thr
            20

(2) INFORMATION FOR SEQ ID NO: 91:

(i) SEQUENCE CHARACTERISTICS:
            (A) LENGTH:               52 amino acids
            (B) TYPE:                 amino acid
            (C) STRANDEDNESS:         single
            (D) TOPOLOGY:             linear (ii) MOLECULE TYPE:             peptide (xi) SEQUENCE DESCRIPTION: SEQ ID NO: 91:

Gly Arg Pro Arg Ala Ile Asn Lys His Glu Gln Glu Gln Ile Ser Arg
1               5                   10                  15

Leu Leu Glu Lys Gly His Pro Arg Gln Gln Leu Ala Ile Ile Phe Gly
            20                  25                  30

Ile Gly Val Ser Thr Leu Tyr Arg Tyr Phe Pro Ala Ser Ser Ile Lys
            35                  40                  45

Lys Arg Met Asn
      50

(2) INFORMATION FOR SEQ ID NO: 92:

(i) SEQUENCE CHARACTERISTICS:
            (A) LENGTH:               18 amino acids
            (B) TYPE:                 amino acid
            (C) STRANDEDNESS:         single
            (D) TOPOLOGY:             linear (ii) MOLECULE TYPE:             peptide (xi) SEQUENCE DESCRIPTION: SEQ ID NO: 92:

Lys Ser Gly Pro Arg Pro Arg Gly Thr Arg Gly Lys Gly Arg Arg Ile
1               5                   10                  15

Arg Arg (2) INFORMATION FOR SEQ ID NO: 93:

(i) SEQUENCE CHARACTERISTICS:

```
              (A) LENGTH:              12 amino acids
              (B) TYPE:                amino acid
              (C) STRANDEDNESS:        single
              (D) TOPOLOGY:            linear (ii) MOLECULE TYPE:           peptide (xi) SEQUENCE DESCRIPTION: SEQ ID NO: 93:

Lys Asp Arg Ser Asn Leu Leu Glu Arg His Thr Arg
 1               5                  10

(2) INFORMATION FOR SEQ ID NO: 94:

(i) SEQUENCE CHARACTERISTICS:
              (A) LENGTH:              16 amino acids
              (B) TYPE:                amino acid
              (C) STRANDEDNESS:        single
              (D) TOPOLOGY:            linear (ii) MOLECULE TYPE:           peptide (xi) SEQUENCE DESCRIPTION: SEQ ID NO: 94:

Lys Arg Pro Ala Ala Thr Lys Lys Ala Gly Gln Ala Lys Lys Lys Leu
 1               5                  10                  15

(2) INFORMATION FOR SEQ ID NO: 95:

(i) SEQUENCE CHARACTERISTICS:
              (A) LENGTH:              7 amino acids
              (B) TYPE:                amino acid
              (C) STRANDEDNESS:        single
              (D) TOPOLOGY:            linear (ii) MOLECULE TYPE:           peptide (xi) SEQUENCE DESCRIPTION: SEQ ID NO: 95:

Lys Lys Lys Lys Lys Trp Lys
 1               5

(2) INFORMATION FOR SEQ ID NO: 96:

(i) SEQUENCE CHARACTERISTICS:
              (A) LENGTH:              8 amino acids
              (B) TYPE:                amino acid
              (C) STRANDEDNESS:        single
              (D) TOPOLOGY:            linear (ii) MOLECULE TYPE:           peptide (xi) SEQUENCE DESCRIPTION: SEQ ID NO: 96:

Lys Lys Lys Lys Lys Lys Trp Lys
 1               5

(2) INFORMATION FOR SEQ ID NO: 97:

(i) SEQUENCE CHARACTERISTICS:
              (A) LENGTH:              9 amino acids
              (B) TYPE:                amino acid
              (C) STRANDEDNESS:        single
              (D) TOPOLOGY:            linear (ii) MOLECULE TYPE:           peptide (xi) SEQUENCE DESCRIPTION: SEQ ID NO: 97:

Lys Lys Lys Lys Lys Lys Lys Trp Lys
 1               5

(2) INFORMATION FOR SEQ ID NO: 98:
```

```
        (i) SEQUENCE CHARACTERISTICS:
             (A) LENGTH:          10 amino acids
             (B) TYPE:            amino acid
             (C) STRANDEDNESS:    single
             (D) TOPOLOGY:        linear (ii) MOLECULE TYPE:         peptide (xi) SEQUENCE DESCRIPTION: SEQ ID NO: 98:

Lys Lys Lys Lys Lys Lys Lys Lys Trp Lys
 1               5                  10

(2) INFORMATION FOR SEQ ID NO: 99:

(i) SEQUENCE CHARACTERISTICS:
             (A) LENGTH:          11 amino acids
             (B) TYPE:            amino acid
             (C) STRANDEDNESS:    single
             (D) TOPOLOGY:        linear (ii) MOLECULE TYPE:         peptide (xi) SEQUENCE DESCRIPTION: SEQ ID NO: 99:

Lys Lys Lys Lys Lys Lys Lys Lys Lys Trp Lys
 1               5                  10

(2) INFORMATION FOR SEQ ID NO: 100:

(i) SEQUENCE CHARACTERISTICS:
             (A) LENGTH:          12 amino acids
             (B) TYPE:            amino acid
             (C) STRANDEDNESS:    single
             (D) TOPOLOGY:        linear (ii) MOLECULE TYPE:         peptide (xi) SEQUENCE DESCRIPTION: SEQ ID NO: 100:

Lys Lys Lys Lys Lys Lys Lys Lys Lys Lys Trp Lys
 1               5                  10

(2) INFORMATION FOR SEQ ID NO: 101:

(i) SEQUENCE CHARACTERISTICS:
             (A) LENGTH:          13 amino acids
             (B) TYPE:            amino acid
             (C) STRANDEDNESS:    single
             (D) TOPOLOGY:        linear (ii) MOLECULE TYPE:         peptide (xi) SEQUENCE DESCRIPTION: SEQ ID NO: 101:

Lys Lys Lys Lys Lys Lys Lys Lys Lys Lys Lys Trp Lys
 1               5                  10

(2) INFORMATION FOR SEQ ID NO: 102:

(i) SEQUENCE CHARACTERISTICS:
             (A) LENGTH:          14 amino acids
             (B) TYPE:            amino acid
             (C) STRANDEDNESS:    single
             (D) TOPOLOGY:        linear (ii) MOLECULE TYPE:         peptide (xi) SEQUENCE DESCRIPTION: SEQ ID NO: 102:

Lys Lys Lys Lys Lys Lys Lys Lys Lys Lys Lys Lys Trp Lys
 1               5                  10

(2) INFORMATION FOR SEQ ID NO: 103:
```

(i) SEQUENCE CHARACTERISTICS:
    (A) LENGTH:          15 amino acids
    (B) TYPE:            amino acid
    (C) STRANDEDNESS:    single
    (D) TOPOLOGY:        linear (ii) MOLECULE TYPE:        peptide (xi) SEQUENCE DESCRIPTION: SEQ ID NO: 103:

```
Lys Lys Lys Lys Lys Lys Lys Lys Lys Lys Lys Lys Lys Trp Lys
 1               5                  10                  15
```

(2) INFORMATION FOR SEQ ID NO: 104:

(i) SEQUENCE CHARACTERISTICS:
        (A) LENGTH:          16 amino acids
        (B) TYPE:            amino acid
        (C) STRANDEDNESS:    single
        (D) TOPOLOGY:        linear (ii) MOLECULE TYPE:        peptide (xi) SEQUENCE DESCRIPTION: SEQ ID NO: 104:

```
Lys Lys Lys Lys Lys Lys Lys Lys Lys Lys Lys Lys Lys Lys Trp Lys
 1               5                  10                  15
```

(2) INFORMATION FOR SEQ ID NO: 105:

(i) SEQUENCE CHARACTERISTICS:
        (A) LENGTH:          17 amino acids
        (B) TYPE:            amino acid
        (C) STRANDEDNESS:    single
        (D) TOPOLOGY:        linear (ii) MOLECULE TYPE:        peptide (xi) SEQUENCE DESCRIPTION: SEQ ID NO: 105:

```
Lys Lys Lys Lys Lys Lys Lys Lys Lys Lys Lys Lys Lys Lys Lys Trp
 1               5                  10                  15

Lys
```

(2) INFORMATION FOR SEQ ID NO: 106:

(i) SEQUENCE CHARACTERISTICS:
        (A) LENGTH:          18 amino acids
        (B) TYPE:            amino acid
        (C) STRANDEDNESS:    single
        (D) TOPOLOGY:        linear (ii) MOLECULE TYPE:        peptide (xi) SEQUENCE DESCRIPTION: SEQ ID NO: 106:

```
Lys Lys Lys Lys Lys Lys Lys Lys Lys Lys Lys Lys Lys Lys Lys Lys
 1               5                  10                  15

Trp Lys
```

(2) INFORMATION FOR SEQ ID NO: 107:

(i) SEQUENCE CHARACTERISTICS:
        (A) LENGTH:          19 amino acids
        (B) TYPE:            amino acid
        (C) STRANDEDNESS:    single
        (D) TOPOLOGY:        linear (ii) MOLECULE TYPE:        peptide (xi) SEQUENCE DESCRIPTION: SEQ ID NO: 107:

```
Lys Lys Lys Lys Lys Lys Lys Lys Lys Lys Lys Lys Lys Lys Lys
1               5                   10                  15

Lys Trp Lys (2) INFORMATION FOR SEQ ID NO: 108:

(i) SEQUENCE CHARACTERISTICS:
        (A) LENGTH:           20 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 108:

Lys Lys Lys Lys Lys Lys Lys Lys Lys Lys Lys Lys Lys Lys Lys
1               5                   10                  15

Lys Lys Trp Lys
        20

(2) INFORMATION FOR SEQ ID NO: 109:

(i) SEQUENCE CHARACTERISTICS:
        (A) LENGTH:           21 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 109:

Lys Lys Lys Lys Lys Lys Lys Lys Lys Lys Lys Lys Lys Lys Lys
1               5                   10                  15

Lys Lys Lys Trp Lys
            20

(2) INFORMATION FOR SEQ ID NO: 110:

(i) SEQUENCE CHARACTERISTICS:
        (A) LENGTH:           22 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 110:

Lys Lys Lys Lys Lys Lys Lys Lys Lys Lys Lys Lys Lys Lys Lys
1               5                   10                  15

Lys Lys Lys Lys Trp Lys
                20

(2) INFORMATION FOR SEQ ID NO: 111:

(i) SEQUENCE CHARACTERISTICS:
        (A) LENGTH:           23 amino acids
        (B) TYPE:             amino acid
        (C) STRANDEDNESS:     single
        (D) TOPOLOGY:         linear (ii) MOLECULE TYPE:       peptide (xi) SEQUENCE DESCRIPTION: SEQ ID NO: 111:

Lys Lys Lys Lys Lys Lys Lys Lys Lys Lys Lys Lys Lys Lys Lys
1               5                   10                  15

Lys Lys Lys Lys Lys Trp Lys
```

20

(2) INFORMATION FOR SEQ ID NO: 112:

(i) SEQUENCE CHARACTERISTICS:
  (A) LENGTH:   24 amino acids
  (B) TYPE:    amino acid
  (C) STRANDEDNESS: single
  (D) TOPOLOGY:  linear (ii) MOLECULE TYPE:  peptide (xi) SEQUENCE DESCRIPTION: SEQ ID NO: 112:

```
Lys Lys Lys Lys Lys Lys Lys Lys Lys Lys Lys Lys Lys Lys Lys Lys
 1               5                  10                  15
Lys Lys Lys Lys Lys Lys Trp Lys
            20
```

(2) INFORMATION FOR SEQ ID NO: 113:

(i) SEQUENCE CHARACTERISTICS:
  (A) LENGTH:   25 amino acids
  (B) TYPE:    amino acid
  (C) STRANDEDNESS: single
  (D) TOPOLOGY:  linear (ii) MOLECULE TYPE:  peptide (xi) SEQUENCE DESCRIPTION: SEQ ID NO: 113:

```
Lys Lys Lys Lys Lys Lys Lys Lys Lys Lys Lys Lys Lys Lys Lys Lys
 1               5                  10                  15
Lys Lys Lys Lys Lys Lys Lys Trp Lys
            20                  25
```

(2) INFORMATION FOR SEQ ID NO: 114:

(i) SEQUENCE CHARACTERISTICS:
  (A) LENGTH:   26 amino acids
  (B) TYPE:    amino acid
  (C) STRANDEDNESS: single
  (D) TOPOLOGY:  linear (ii) MOLECULE TYPE:  peptide (xi) SEQUENCE DESCRIPTION: SEQ ID NO: 114:

```
Lys Lys Lys Lys Lys Lys Lys Lys Lys Lys Lys Lys Lys Lys Lys Lys
 1               5                  10                  15
Lys Lys Lys Lys Lys Lys Lys Lys Trp Lys
            20                  25
```

(2) INFORMATION FOR SEQ ID NO: 115:

(i) SEQUENCE CHARACTERISTICS:
  (A) LENGTH:   27 amino acids
  (B) TYPE:    amino acid
  (C) STRANDEDNESS: single
  (D) TOPOLOGY:  linear (ii) MOLECULE TYPE:  peptide (xi) SEQUENCE DESCRIPTION: SEQ ID NO: 115:

```
Lys Lys Lys Lys Lys Lys Lys Lys Lys Lys Lys Lys Lys Lys Lys Lys
 1               5                  10                  15
Lys Lys Lys Lys Lys Lys Lys Lys Lys Trp Lys
            20                  25
```

(2) INFORMATION FOR SEQ ID NO: 116:

(i) SEQUENCE CHARACTERISTICS:
        (A) LENGTH:         28 amino acids
        (B) TYPE:           amino acid
        (C) STRANDEDNESS:   single
        (D) TOPOLOGY:       linear (ii) MOLECULE TYPE:     peptide (xi) SEQUENCE DESCRIPTION: SEQ ID NO: 116:

Lys Lys Lys Lys Lys Lys Lys Lys Lys Lys Lys Lys Lys Lys Lys
 1               5                  10                  15
Lys Lys Lys Lys Lys Lys Lys Lys Lys Lys Trp Lys
            20                  25

(2) INFORMATION FOR SEQ ID NO: 117:

(i) SEQUENCE CHARACTERISTICS:
        (A) LENGTH:         29 amino acids
        (B) TYPE:           amino acid
        (C) STRANDEDNESS:   single
        (D) TOPOLOGY:       linear (ii) MOLECULE TYPE:     peptide (xi) SEQUENCE DESCRIPTION: SEQ ID NO: 117:

Lys Lys Lys Lys Lys Lys Lys Lys Lys Lys Lys Lys Lys Lys Lys
 1               5                  10                  15
Lys Lys Lys Lys Lys Lys Lys Lys Lys Lys Lys Trp Lys
            20                  25

(2) INFORMATION FOR SEQ ID NO: 118:

(i) SEQUENCE CHARACTERISTICS:
        (A) LENGTH:         30 amino acids
        (B) TYPE:           amino acid
        (C) STRANDEDNESS:   single
        (D) TOPOLOGY:       linear (ii) MOLECULE TYPE:     peptide (xi) SEQUENCE DESCRIPTION: SEQ ID NO: 118:

Lys Lys Lys Lys Lys Lys Lys Lys Lys Lys Lys Lys Lys Lys Lys
 1               5                  10                  15
Lys Lys Lys Lys Lys Lys Lys Lys Lys Lys Lys Lys Trp Lys
            20                  25                  30

(2) INFORMATION FOR SEQ ID NO: 119:

(i) SEQUENCE CHARACTERISTICS:
        (A) LENGTH:         31 amino acids
        (B) TYPE:           amino acid
        (C) STRANDEDNESS:   single
        (D) TOPOLOGY:       linear (ii) MOLECULE TYPE:     peptide (xi) SEQUENCE DESCRIPTION: SEQ ID NO: 119:

Lys Lys Lys Lys Lys Lys Lys Lys Lys Lys Lys Lys Lys Lys Lys
 1               5                  10                  15
Lys Lys Lys Lys Lys Lys Lys Lys Lys Lys Lys Lys Lys Trp Lys
            20                  25                  30

(2) INFORMATION FOR SEQ ID NO: 120:

(i) SEQUENCE CHARACTERISTICS:

```
            (A) LENGTH:              32 amino acids
            (B) TYPE:                amino acid
            (C) STRANDEDNESS:        single
            (D) TOPOLOGY:            linear (ii) MOLECULE TYPE:            peptide (xi) SEQUENCE DESCRIPTION: SEQ ID NO: 120:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Trp Lys
            20                  25                  30

(2) INFORMATION FOR SEQ ID NO: 121:

(i) SEQUENCE CHARACTERISTICS:
            (A) LENGTH:              33 amino acids
            (B) TYPE:                amino acid
            (C) STRANDEDNESS:        single
            (D) TOPOLOGY:            linear (ii) MOLECULE TYPE:            peptide (xi) SEQUENCE DESCRIPTION: SEQ ID NO: 121:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Trp
            20                  25                  30

Lys (2) INFORMATION FOR SEQ ID NO: 122:

(i) SEQUENCE CHARACTERISTICS:
            (A) LENGTH:              34 amino acids
            (B) TYPE:                amino acid
            (C) STRANDEDNESS:        single
            (D) TOPOLOGY:            linear (ii) MOLECULE TYPE:            peptide (xi) SEQUENCE DESCRIPTION: SEQ ID NO: 122:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Trp Lys (2) INFORMATION FOR SEQ ID NO: 123:

(i) SEQUENCE CHARACTERISTICS:
            (A) LENGTH:              35 amino acids
            (B) TYPE:                amino acid
            (C) STRANDEDNESS:        single
            (D) TOPOLOGY:            linear (ii) MOLECULE TYPE:            peptide (xi) SEQUENCE DESCRIPTION: SEQ ID NO: 123:

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Trp Lys
    35
```

(2) INFORMATION FOR SEQ ID NO: 124:

(i) SEQUENCE CHARACTERISTICS:
        (A) LENGTH:        36 amino acids
        (B) TYPE:          amino acid
        (C) STRANDEDNESS:  single
        (D) TOPOLOGY:     linear (ii) MOLECULE TYPE:      peptide (xi) SEQUENCE DESCRIPTION: SEQ ID NO: 124:

```
Lys Lys Lys Lys Lys Lys Lys Lys Lys Lys Lys Lys Lys Lys Lys Lys
 1               5                  10                  15
Lys Lys Lys Lys Lys Lys Lys Lys Lys Lys Lys Lys Lys Lys Lys
            20                  25                  30
Lys Lys Trp Lys
        35
```

(2) INFORMATION FOR SEQ ID NO: 125:

(i) SEQUENCE CHARACTERISTICS:
        (A) LENGTH:        37 amino acids
        (B) TYPE:          amino acid
        (C) STRANDEDNESS:  single
        (D) TOPOLOGY:     linear (ii) MOLECULE TYPE:      peptide (xi) SEQUENCE DESCRIPTION: SEQ ID NO: 125:

```
Lys Lys Lys Lys Lys Lys Lys Lys Lys Lys Lys Lys Lys Lys Lys Lys
 1               5                  10                  15
Lys Lys Lys Lys Lys Lys Lys Lys Lys Lys Lys Lys Lys Lys Lys
            20                  25                  30
Lys Lys Lys Trp Lys
        35
```

(2) INFORMATION FOR SEQ ID NO: 126:

(i) SEQUENCE CHARACTERISTICS:
        (A) LENGTH:        38 amino acids
        (B) TYPE:          amino acid
        (C) STRANDEDNESS:  single
        (D) TOPOLOGY:     linear (ii) MOLECULE TYPE:      peptide (xi) SEQUENCE DESCRIPTION: SEQ ID NO: 126:

```
Lys Lys Lys Lys Lys Lys Lys Lys Lys Lys Lys Lys Lys Lys Lys Lys
 1               5                  10                  15
Lys Lys Lys Lys Lys Lys Lys Lys Lys Lys Lys Lys Lys Lys Lys Lys
            20                  25                  30
Lys Lys Lys Lys Trp Lys
        35
```

(2) INFORMATION FOR SEQ ID NO: 127:

(i) SEQUENCE CHARACTERISTICS:
        (A) LENGTH:        39 amino acids
        (B) TYPE:          amino acid
        (C) STRANDEDNESS:  single
        (D) TOPOLOGY:     linear (ii) MOLECULE TYPE:      peptide (xi) SEQUENCE DESCRIPTION: SEQ ID NO: 127:

```
Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
                20                  25                  30

Lys Lys Lys Lys Lys Trp Lys
        35
```

(2) INFORMATION FOR SEQ ID NO: 128:

(i) SEQUENCE CHARACTERISTICS:
        (A) LENGTH:         40 amino acids
        (B) TYPE:           amino acid
        (C) STRANDEDNESS:   single
        (D) TOPOLOGY:      linear (ii) MOLECULE TYPE:      peptide (xi) SEQUENCE DESCRIPTION: SEQ ID NO: 128:

```
Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
                20                  25                  30

Lys Lys Lys Lys Lys Lys Trp Lys
        35                  40
```

(2) INFORMATION FOR SEQ ID NO: 129:

(i) SEQUENCE CHARACTERISTICS:
        (A) LENGTH:         41 amino acids
        (B) TYPE:           amino acid
        (C) STRANDEDNESS:   single
        (D) TOPOLOGY:      linear (ii) MOLECULE TYPE:      peptide (xi) SEQUENCE DESCRIPTION: SEQ ID NO: 129:

```
Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
                20                  25                  30

Lys Lys Lys Lys Lys Lys Lys Trp Lys
        35                  40
```

(2) INFORMATION FOR SEQ ID NO: 130:

(i) SEQUENCE CHARACTERISTICS:
        (A) LENGTH:         42 amino acids
        (B) TYPE:           amino acid
        (C) STRANDEDNESS:   single
        (D) TOPOLOGY:      linear (ii) MOLECULE TYPE:      peptide (xi) SEQUENCE DESCRIPTION: SEQ ID NO: 130:

```
Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
                20                  25                  30

Lys Lys Lys Lys Lys Lys Lys Lys Trp Lys
        35                  40
```

(2) INFORMATION FOR SEQ ID NO: 131:

(i) SEQUENCE CHARACTERISTICS:

```
              (A) LENGTH:               43 amino acids
              (B) TYPE:                 amino acid
              (C) STRANDEDNESS:         single
              (D) TOPOLOGY:             linear (ii) MOLECULE TYPE:            peptide (xi) SEQUENCE DESCRIPTION: SEQ ID NO:  131:

Lys Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys Lys
            20                  25                  30

Lys Lys Lys Lys Lys Lys Lys Lys Trp Lys
        35                  40

(2) INFORMATION FOR SEQ ID NO:  132:

(i) SEQUENCE CHARACTERISTICS:
              (A) LENGTH:               27 amino acids
              (B) TYPE:                 amino acid
              (C) STRANDEDNESS:         single
              (D) TOPOLOGY:             linear (ii) MOLECULE TYPE:            peptide (xi) SEQUENCE DESCRIPTION: SEQ ID NO:  132:

Lys Ser Pro Leu Leu Lys Ser Met Lys Gly Ile Lys Gln Gln Gln His
 1               5                  10                  15

Pro Ser Pro Asn Gln Gln Gln His Pro Gly Lys
            20                  25

2) INFORMATION FOR SEQ ID NO:  133:

(i) SEQUENCE CHARACTERISTICS:
              (A) LENGTH:               35 amino acids
              (B) TYPE:                 amino acid
              (C) STRANDEDNESS:         single
              (D) TOPOLOGY:             linear (ii) MOLECULE TYPE:            peptide (xi) SEQUENCE DESCRIPTION: SEQ ID NO:  133:

Lys Ser Pro Leu Leu Lys Ser Met Lys Gly Ile Lys Gln Gln Gln His
 1               5                  10                  15

Pro Ser Pro Asn Gln Gln Gln His Pro Ser Pro Asn Gln Gln Gln His
            20                  25                  30

Pro Gly Lys
        35

(2) INFORMATION FOR SEQ ID NO:  134:

(i) SEQUENCE CHARACTERISTICS:
              (A) LENGTH:               43 amino acids
              (B) TYPE:                 amino acid
              (C) STRANDEDNESS:         single
              (D) TOPOLOGY:             linear (ii) MOLECULE TYPE:            peptide (xi) SEQUENCE DESCRIPTION: SEQ ID NO:  134:

Lys Ser Pro Leu Leu Lys Ser Met Lys Gly Ile Lys Gln Gln Gln His
 1               5                  10                  15

Pro Ser Pro Asn Gln Gln Gln His Pro Ser Pro Asn Gln Gln Gln His
            20                  25                  30

Pro Ser Pro Asn Gln Gln Gln His Pro Gly Lys
```

(2) INFORMATION FOR SEQ ID NO: 135:

(i) SEQUENCE CHARACTERISTICS:
      (A) LENGTH:           51 amino acids
      (B) TYPE:             amino acid
      (C) STRANDEDNESS:     single
      (D) TOPOLOGY:         linear (ii) MOLECULE TYPE:      peptide (xi) SEQUENCE DESCRIPTION: SEQ ID NO: 135:

Lys Ser Pro Leu Leu Lys Ser Met Lys Gly Ile Lys Gln Gln Gln His
 1               5                  10                  15

Pro Ser Pro Asn Gln Gln Gln His Pro Ser Pro Asn Gln Gln Gln His
            20                  25                  30

Pro Ser Pro Asn Gln Gln Gln His Pro Ser Pro Asn Gln Gln Gln His
        35                  40                  45

Pro Gly Lys
    50

(2) INFORMATION FOR SEQ ID NO: 136:

(i) SEQUENCE CHARACTERISTICS:
      (A) LENGTH:           59 amino acids
      (B) TYPE:             amino acid
      (C) STRANDEDNESS:     single
      (D) TOPOLOGY:         linear (ii) MOLECULE TYPE:      peptide (xi) SEQUENCE DESCRIPTION: SEQ ID NO: 136:

Lys Ser Pro Leu Leu Lys Ser Met Lys Gly Ile Lys Gln Gln Gln His
 1               5                  10                  15

Pro Ser Pro Asn Gln Gln Gln His Pro Ser Pro Asn Gln Gln Gln His
            20                  25                  30

Pro Ser Pro Asn Gln Gln Gln His Pro Ser Pro Asn Gln Gln Gln His
        35                  40                  45

Pro Ser Pro Asn Gln Gln Gln His Pro Gly Lys
    50                  55

(2) INFORMATION FOR SEQ ID NO: 137:

(i) SEQUENCE CHARACTERISTICS:
      (A) LENGTH:           67 amino acids
      (B) TYPE:             amino acid
      (C) STRANDEDNESS:     single
      (D) TOPOLOGY:         linear (ii) MOLECULE TYPE:      peptide (xi) SEQUENCE DESCRIPTION: SEQ ID NO: 137:

Lys Ser Pro Leu Leu Lys Ser Met Lys Gly Ile Lys Gln Gln Gln His
 1               5                  10                  15

Pro Ser Pro Asn Gln Gln Gln His Pro Ser Pro Asn Gln Gln Gln His
            20                  25                  30

Pro Ser Pro Asn Gln Gln Gln His Pro Ser Pro Asn Gln Gln Gln His
        35                  40                  45

Pro Ser Pro Asn Gln Gln Gln His Pro Ser Pro Asn Gln Gln Gln His
    50                  55                  60

Pro Gly Lys
65

(2) INFORMATION FOR SEQ ID NO: 138:

(i) SEQUENCE CHARACTERISTICS:
        (A) LENGTH:          20 amino acids
        (B) TYPE:            amino acid
        (C) STRANDEDNESS:    single
        (D) TOPOLOGY:        linear (ii) MOLECULE TYPE:       peptide (xi) SEQUENCE DESCRIPTION: SEQ ID NO: 138:

Gly Leu Phe Glu Ala Leu Leu Glu Leu Leu Glu Ser Leu Trp Glu Leu
1            5                    10                15

Leu Leu Glu Ala
          20

(2) INFORMATION FOR SEQ ID NO: 139:

(i) SEQUENCE CHARACTERISTICS:
        (A) LENGTH:          11 amino acids
        (B) TYPE:            amino acid
        (C) STRANDEDNESS:    single
        (D) TOPOLOGY:        linear (ii) MOLECULE TYPE:       peptide (xi) SEQUENCE DESCRIPTION: SEQ ID NO: 139:

Gly Leu Phe Lys Leu Leu Glu Glu Trp Leu Glu
1            5                    10

LIPOPHILIC PEPTIDES FOR MACROMOLECULE DELIVERY

The invention described herein was developed in part with funds provided by the United States Public Health Service of the Department of Health and Human Services, Grant Number HL-360147. The Government has certain rights.

FIELD OF THE INVENTION

The present invention relates generally to the field of delivering agents, including genes and other biological macromolecules, to cells.

BACKGROUND OF THE INVENTION

The following description of the background of the invention is provided to aid in understanding the claimed invention, but it is not admitted to constitute or describe prior art to the claimed invention and should in no way be construed as limiting the claimed invention.

Several techniques currently exist for delivering genes to cells and many clinical trials are currently ongoing in order to evaluate the degree of therapeutic efficacy obtained using such methods. One method of gene delivery involves the use of recombinant retroviral vectors for delivery of genes to cells of living animals. Morgan et al., *Annu. Rev. Biochem.*, 62:191–217 (1993). Retroviral vectors permanently integrate the transferred gene into the host chromosomal DNA. In addition to retroviruses, other virus have been used for gene delivery. Adenoviruses have been developed as a means for gene transfer into epithelial derived tissues. Stratford-Perricaudet et al., *Hum. Gene. Ther.,* 1:241–256 (1990); Gilardi et al., *FEBS*, 267:60–62 (1990); Rosenfeld et al., *Science*, 252:4341–4346 (1991); Morgan et al., *Annu. Rev. Biochem.*, 62:191–217 (1993). Recombinant adenoviral vectors have the advantage over retroviruses of being able to transduce nonproliferating cells, as well as an ability to produce purified high titer virus.

In addition to viral-mediated gene delivery, a more recent means for DNA delivery has been receptor-mediated endocytosis. Endocytosis is the process by which eucaryotic cells continually ingest segments of the plasma membrane in the form of small endocytotic vesicles. Alberts et al., *Mol. Biol. Cell,* Garland Publishing Co., New York, 1983. Extracellular fluid and material dissolved in it becomes trapped in the vesicle and is ingested into the cell. Id. This process of bulk fluid-phase endocytosis can be visualized and quantified using a tracer such as enzyme peroxidase introduced into the extracellular fluid. Id.

Taking advantage of receptor-mediated endocytosis, the asialoglycoprotein receptor has been used in targeting DNA to HepG2 cells in vitro and liver cells in vivo. Wu et al., *J. Biol. Chem.,* 262:4429–4432 (1987); Wu et al., *Bio.,* 27:887–892 (1988); Wu et al., *J. Biol. Chem.,* 263:14620–14624 (1988); Wu et al., *J. Biol. Chem.,* 264:16985–16987 (1989); Wu et al., *J. Biol. Chem.,* 266:14338–14342 (1991). These studies used asialoorosomucoid covalently linked to polylysine with water soluble carbodiimide, 1-ethyl-3-(3-dimethylaminopropyl)-carbodiimide or with 3'(2'pyridyl-dithio)propionic acid n-hydroxysuccinimide ester. Polylysine in the studies above bound DNA through ionic interaction. The DNA was ingested by endocytosis.

Other studies have utilized transferrin and the transferrin receptor for delivery of DNA to cells in vitro. Wagner et al., *P.N.A.S.,* 87:3410–3414 (1990). These studies modified transferrin by covalently coupling transferrin to polylysine. Id. The polylysine interacted ionically with DNA. Delivery of DNA occurred to cells through the transferrin receptor. Such analyses were performed in vitro. Id. Cotten et al., *P.N.A.S.,* 87:4033–4037 (1990); Zenk et al., *P.N.A.S.,* 87:3655–3659 (1990).

In addition to delivery DNA (Gottschalk et al.,Gene Therapy 1:185–91 (1993)), other macromolecules can also be delivered by receptor-ligand systems. Leamon et al., *P.N.A.S.,* 88:5572–5576 (1991); Leamon et al., *J. Biol. Chem., 267:24966–24971* (1992). In particular these studies have involved the folate receptor, an anchored glycosyl-phosphatidyl protein, which is excluded from coated pits and cycles in and out of the cells by caveolae. Anderson et al., *Science,* 252:410–411 (1992). This uptake mechanism has been called potocytosis. Id. Folate conjugated enzymes have been delivered into cells through this receptor system and retained activity for at least six hours. Leamon et al., *P.N.A.S.,* 88:5572–5576 (1991). Folate receptors have limited tissue distribution and are overexpressed in several malignant cell lines derived from many tissues. Weitman et al., *Cancer Res.,* 52:3396–3401 (1992); Weitman et al., *Cancer Res.,* 52:6708–6711 (1992); Campbell, *Cancer Res.,* 51:5329–5338 (1991); Coney, *Cancer Res.,* 51:6125–6123 (1991). Other studies have also used biotin or folate conjugated to proteins by biotinylation for protein delivery to the cell. Low et al., U.S. Pat. No. 5,108,921.

Nucleic Acid Transporters for Delivery of Nucleic Acids into a Cell; Smith et al., U.S. patent application Ser. No. 08/484,777, filed Dec. 18, 1995, incorporated herein by reference in its entirety including any drawings.

A non-exchangeable apolipoprotein E peptide that mediates binding to the low density lipoprotein receptor is described in Mims et al., Journal of Biological Chemistry, 269 (32) 20539–20547, 1994, incorporated herein by reference in its entirety, including any drawings.

SUMMARY OF THE INVENTION

The present invention provides novel uses of lipophilic peptides for delivering macromolecules (e.g. nucleic acids) into a cell, complexes formed between the macromolecules to be delivered and the lipophilic peptide, and cells transformed by such complexes. Thus, the present invention allows for enhanced delivery of macromolecules (including nucleic acids) into cells.

The lipophilic peptide has a delivery peptide portion and a lipid moiety portion. The amino acid sequences of several suitable delivery peptides are set forth herein and those skilled in the art would be able to make and use many others given the methods described herein. The lipid moiety makes the delivery peptide lipophilic and examples of suitable modifications are provided herein. Again, however, those skilled in the art would be able to make and use lipophilic peptides having different lipid moieties.

Thus, in a first aspect, the present invention features a peptide-macromolecule complex for delivering a macromolecule into a cell. The complex includes a lipophilic peptide having a delivery peptide associated with a lipid moiety. The delivery peptide portion of the lipophilic peptide is complexed to the macromolecule.

The term "peptide-macromolecule complex" as used herein refers to a molecular complex which is capable of transporting a macromolecule through the cell membrane. This molecular complex is preferably bound to a macromolecule noncovalently. The peptide-macromolecule complex should be capable of transporting nucleic acid in a stable and condensed state and of releasing the noncovalently bound nucleic acid into the cellular interior. Furthermore, the nucleic acid carrier may prevent lysosomal degradation of the nucleic acid by endosomal lysis. In addition, although not necessary, the peptide-macromolecule complex can also efficiently transport the nucleic acid through the nuclear membrane, as discussed below.

The peptide-macromolecule complex as described herein can contain, but is not limited to, seven components. It comprises, consists or consists essentially of: (1) a nucleic acid or other macromolecule with a known primary sequence that contains the genetic information of interest or a known chemical composition; (2) a peptide agent capable of stabilizing and condensing the nucleic acid or macromolecule in (1) above; (3) an N termini acylation moiety to increase the lipophilicity of the peptide agent in (2) above (4) a lysis moiety that enables the transport of the entire complex from the cell surface directly into the cytoplasm of the cell; (5) a moiety that recognizes and binds to a cell surface receptor or antigen or is capable of entering a cell through cytosis; (6) a moiety that is capable of moving or initiating movement through a nuclear membrane; and/or (7) a nucleic acid or macromolecular molecule binding moiety capable of covalently binding the moieties of (2), (3), (4), (5), and (6) above.

The term "delivery" refers to transportation of a molecule to a desired cell or any cell. Delivery can be to the cell surface, cell membrane, cell endosome, within the cell membrane, nucleus or within the nucleus, or any other desired area of the cell. Delivery includes not only transporting nucleic acid but also other macromolecules including, but not limited to, proteins, lipids, carbohydrates and various other molecules.

The term "macromolecule", refers to any natural and/or synthetic polymeric molecule capable of being in a biological environment and includes but is not limited to, proteins, oligonucleotides, dextrans, lipids or carbohydrates that can be delivered using the complexes or carrier systems described herein. The term "nucleic acid" as used herein refers to DNA or RNA. This would include naked DNA, a nucleic acid cassette, naked RNA, or nucleic acid contained in vectors or viruses. These are only examples and are not meant to be limiting.

A variety of proteins and polypeptides can be encoded by the nucleic acid. Those proteins or polypeptides which can be expressed include hormones, growth factors, enzymes, clotting factors, apolipoproteins, receptors, drugs, oncogenes, tumor antigens, tumor suppressors, cytokines, viral antigens, parasitic antigens, bacterial antigens and chemically synthesized polymers and polymers biosynthesized and/or modified by chemical, cellular and/or enzymatic processes. Specific examples of these compounds include proinsulin, insulin, growth hormone, androgen receptors, insulin-like growth factor I, insulin-like growth factor II, insulin growth factor binding proteins, epidermal growth factor, TGF-$\alpha$, TGF-$\beta$, dermal growth factor (PDGF), angiogenesis factors (acidic fibroblast growth factor, basic fibroblast growth factor and angiogenin), matrix proteins (Type IV collagen, Type VII collagen, laminin), oncogenes (ras, fos, myc, erb, src, sis, jun), E6 or E7 transforming sequence, p53 protein, cytokine receptor, IL-1, IL-6, IL-8, IL-2, $\alpha$, $\beta$, or $\gamma$IFN, GMCSF, GCSF, viral capsid protein, and proteins from viral, bacterial and parasitic organisms. Other specific proteins or polypeptides which can be expressed include: phenylalanine hydroxylase, $\alpha$-1-antitrypsin, cholesterol-7$\alpha$-hydroxylase, truncated apolipoprotein B, lipoprotein lipase, apolipoprotein E, apolipoprotein A1, LDL receptor, molecular variants of each, and combinations thereof. One skilled in the art readily appreciates that these proteins belong to a wide variety of classes of proteins, and that other proteins within these classes can also be used. These are only examples and are not meant to be limiting in any way.

It should also be noted that the genetic material which is incorporated into the cells from the above peptide-macromolecule complex includes (1) nucleic acid not normally found in the cells; (2) nucleic acid which is normally found in the cells but not expressed at physiological significant levels; (3) nucleic acid normally found in the cells and normally expressed at physiological desired levels; (4) other nucleic acid which can be modified for expression in cells; and (5) any combination of the above.

The term "lipophilic peptide" as used herein refers to a peptide which is capable of stabilizing and condensing nucleic acid or a molecule, compound, or protein capable of achieving the same or substantially similar functional characteristics. This will include, but is not limited to, components which are capable of stabilizing and/or condensing nucleic acid by electrostatic binding, hydrophobic binding, hydrogen binding, intercalation or forming helical structures with the nucleic acid, including interaction in the major and/or minor grove of DNA. The term lipophilic peptides can also be referred herein as condensing agent. The lipophilic peptide is capable of noncovalently binding to nucleic acid. The lipophilic peptide is also capable of associating with a surface ligand, a nuclear ligand, and/or a lysis agent. Lipophilic peptides preferably refers to any peptide whose affinity for lipid surfaces is measured by a dissociation constant of $K_d \sim 10^{-6}$ or less and whose $\alpha$-helicity is ~55% in the presence of lipid. Non-lipophilic peptides have an affinity for lipid surfaces measured by a dissociation constant of $>K_d 10^{-5}$ and $\alpha$-helicity of <40% in the presence of lipid. The term "non-exchangeble lipophilic peptide" as used herein refers to any lipophilic peptide whose affinity for lipid surfaces is measured by a dissociation constant of $\leq K_d 10^{-9}$ and whose $\alpha$-helicity is ~78% in the presence of lipid. The term "$\alpha$-helicity" as used herein refers to the preservation of the $\alpha$-helix conformation of the N terminal domain of the derivatized peptide in the presence of lipid.

In general, parameters that are important for lipophilic peptides include the following. First, the peptide must contain sufficient lysine or arginine residues to permit ionic interaction with the DNA. Second, the peptide must have sufficient length to form a stable helix, eleven or twelve residues, and condense the DNA to small particles, e.g., $K_8$ forms larger particles than apoE3. Third, the peptide helix that forms upon interaction with DNA can be stabilized by leucine zipper formation which gives a condensing agent less susceptible to ionic strength. Finally, the lysine or arginine sequence of the condensing peptide serves as an additional function as a nuclear localization sequence.

By "delivery peptide" is meant any amino acid sequence capable of transporting the macromolecule to the desired location in the body when the delivery peptide is associated with a lipid moiety. In the present invention, the most preferred delivery peptide sequence is found within the peptide apoE-$3^{129-169}$ at residues 142–150. The amino acid sequence of this domain is RKLRKRLLR SEQ ID NO:1. In another preferred embodiment, the lipohilic peptide binding molecule is any peptide with the formula K(K)$_n$VTK, SEQ ID NO:2 to SEQ ID NO:38 where n is 4, 5, 6, 7, 8 and homologues to n is 40. In another preferred embodiment, the lipophilic peptides is any peptide with the formula K(K)$_n$XK, SEQ ID NO:39 to SEQ ID NO:75 where n is 4, 5, 6, 7, 8, and homologues to n is 40 where X is any naturally occurring amino acid and analogues thereof. In preferred embodiments the delivery peptide comprises, consists essentially of, or consists of a sequence set forth below or a functional fragment thereof:

STEELRVRLASHLRKLRKRLLRDADDLQKRLAVY-QAGAREG, SEQ ID NO:76
KKQLKKQLKKQLKQWK, SEQ ID NO:77
KKSPKKSPKKSPKKSWK, SEQ ID NO:78
KRRRRRRRRWR, SEQ ID NO:79
KLSKLEKKWSKLEK, SEQ ID NO:80
KLSKLEKKLSKLEKKWSKLEK, SEQ ID NO:81
KSLKKSLKKSLKKSWK, SEQ ID NO:82
KSTPPKKKRKVEDPKDFPSELLSA, SEQ ID NO:83
KAKKKK-NH-$(CH_2)_2$-SS-$(CH_2)_2$-CO-KKKKWK, SEQ ID NO:84
KIRRRGKNKVAARTCRQRRTDR, SEQ ID NO:85
KXKKXKKKXKKXKWK, (where X is A or S) SEQ ID NO:86
KIRRRGKNKAAARTCRERRRSK, SEQ ID NO:87
KIRRRGKNKVAAQNCRKRKLDQ, SEQ ID NO:88
KIRRRGKNKVAAQNCRKRKLET, SEQ ID NO:89
KRRIRREKNKMAAAKCRNRRRELT, SEQ ID NO:90
GRPRAINKHEQEQISRLLEKGHPRQQLAIIFGIGVST-LYRYFPASSIKKRMN, SEQ ID NO:91
KSGPRPRGTRGKGRRIRR, SEQ ID NO:92
KDRSNLLERHTR, SEQ ID NO:93
KRPAATKKAGQAKKKL, SEQ ID NO:94
K(K)$_n$WK, SEQ ID NO:95 to SEQ ID NO:131 where n is 4, 5, 6, 7, 8 and homologues to n is 40,
K(K)$_n$XK, SEQ ID NO:39 to SEQ ID NO:75 where n is 4, 5, 6, 7, 8, and homologues to n is 40
where X is any naturally occurring amino acid and analogues thereof,
KSPLLKSMKGIKQQQHP-(SPNQQQHP)$_n$GK, SEQ ID NO:132 to SEQ ID NO:137 where n is 1-6.

This would include the use of any subfragments of the above which provide nucleic acid stability and condensing characteristics. Furthermore, this would include any derivatives, analogs or modifications of the above peptides. The above peptides can include lysine or arginine residues for electrostatic binding to nucleic acid. These positively charged amino acids help hold the nucleic acid intact. Other examples include or ornithine, homolysine, homoarginine and 2,4-diaminobutyric acid. The lipophilic peptides can also contain tyrosine which is useful in determining peptide concentration and iodination for tracking purposes in vitro and in vivo. Tryptophan also increases the stability of interaction with the nucleic acid through intercalation. In addition, binding of the peptide to DNA quenches tryptophan fluorescence and allows the kinetics and thermodynamics of complex formation to be determined. The lipophilic peptides can also contain helix forming residues such as tryptophan, alanine, leucine or glutamine. These can act as spacers which allow the cationic residues to adopt an optimal configuration for interaction with the nucleic acid in a helical manner, resulting in a more stable complex. Furthermore, the lipophilic peptides can also include a stabilized cyclic version of any of the above mentioned peptides. Such a cyclic version can be formed by introducing a lactam or disulfide bridge. Likewise, dimers of any of the above mentioned peptides can also be used as a binding moiety.

The term delivery peptide can also encompass any derivatives or peptidomimetics in which the peptide bond or backbone of the peptide has been replaced with a molecular skeleton so that the functional residues of the peptide are preserved, and conformationally constrained, in approximately the correct positions for interaction with the active sites on the original peptide. This substitution may include but is not restricted to any atoms of the delivery peptide such as the O and NH atoms of the peptide backbone or other atoms which are rarely involved in close interactions with the active site. "Peptidomimetics" may encompass any such substitutions resulting in the preservation of the residue interactions which are paramount in the proper functioning of the peptide. For example, one peptidomimetic resulted from the substitution of a non-peptidal architectural spacer (i.e., a benzodiazepine-based β-turn mimetic) so that the functional side-chain residues were positioned so that their C-α atoms could occupy equivalent positions to those occupied in the native peptide. This example is not meant to be limiting. Any such peptidomimetics or analogues are encompassed herein.

By "lipid moiety" is meant any agent capable of attaching to a delivery peptide and that upon attachment imparts lipophilic qualities to the overall lipophilic peptide. This preferably increases the lipophilicity of the delivery peptide. Lipophilicity is measured by the decrease in the dissociation constant of the molecule ($K_d$) after attachment. In preferred embodiments, the lipid moiety is a distearyl derivative selected from the group consisting of: (1) N,N-distearyl-glycyl-; (2) ξ-N,N-distearylglycyl-; and (3) N,N-distearylamidomethyl. Other embodiments of the lipid moiety are straight chain or branched chain alkyl groups containing either 0, 1, 2 to 6 unsaturated bonds, with chain lengths from 6 to 30 carbon atoms. Alternatively, the lipid moiety is a dipalmitoyl derivative selected from the group consisting of: $N^\alpha$, $N^{\epsilon'}$-dipalmitoyl-, and $N^\alpha$, $N^\epsilon$-dipaimitoyl. Other embodiments of the lipid moiety are straight chain or branched chain alkyl groups containing either 0, 1, 2 to 6 unsaturated bonds, with chain lengths from 6 to 30 carbon atoms.

The complex is preferably isolated, purified, or enriched. Thus, the complex or carrier system is present in a state that is not found in nature and that is not possible without human intervention. In other preferred embodiments, the complex is capable of binding with a cell surface receptor, lysing an endosome, and targeting the nucleus of said cell. In order to achieve these functions, the lipophilic peptide and/or lipophilic moiety may be associated with a lysis agent, a surface ligand or a nuclear ligand.

The term "associated with" as used herein refers to binding, attaching, connecting or linking molecules through covalent means or noncovalent means. "Associated with" includes, but is not limited to, a lipophilic peptides associated with a surface ligand, nuclear ligand and/or a lysis agent. In addition, it includes the association of a spacer (discussed below) with the above components.

The term "lysis agent" as used herein refers to a molecule, compound, protein or peptide which is capable of breaking down an endosomal membrane and freeing the contents into the cytoplasm of the cell. The lysis agent can work by: (1) a membrane fusion mechanism, i.e., fusogenic, whereby the lysis agent associates or fuses with the cell membrane to allow the endosomal contents to leak into the cytoplasm; (2) a membrane destabilization mechanism whereby the lysis agent disrupts the structural organization of the cell membrane thereby causing leakage through the endosome into the cytoplasm; or (3) other known or unknown mechanisms which cause endosomal lysis. This term includes, but is not limited to, synthetic compounds such as the JTS-1 peptide, viruses, lytic peptides, or derivatives thereof. The term "lytic peptide" refers to a chemical grouping which penetrates a membrane such that the structural organization and integrity of the membrane is lost. As a result of the presence of the lysis agent, the membrane undergoes lysis, fusion or both.

In the present invention, a preferred lysis agent is the JTS-1 peptide or derivatives thereof. The amino acid sequence of JTS-1 lytic peptide is GLFEALLELLESL-WELLLEA. SEQ ID NO:138. One skilled in the art will readily appreciate and understand that such nomenclature is the standard notation accepted in the art for designating amino acids. The JTS-1 lytic peptide and derivatives are designed as an α-helix, which contains a sequence of amino acids such that the side chains are distributed to yield a peptide with hydrophobic and hydrophilic sides. Such α-helixes are termed amphipathic or amphiphilic. The hydrophobic side contains highly apolar amino acid side chains, both neutral and non-neutral. The hydrophilic side contains an extensive number of glutamic acids but could also contain aspartic acid, as well as polar or basic amino acids. The JTS-1 peptide would include any derivatives or modifications of the backbone thereof. The lytic peptide undergoes secondary structure changes at acidic pH resulting in the formation of oligomeric aggregates which possess selective lytic properties.

In general, parameters that are important for amphiphilic peptide lysis activity include the following. First, Hydrophobicity: The peptide must have a high enough hydrophobicity of the hydrophobic face to interact with and penetrate phospholipid-cholesterol membranes, i.e., lipid binding per se is not sufficient. Red cell hemolysis assays give better indications of which peptides will have useful activity. Second, Peptide aggregation: The ability to aggregate plays an important role in lysis and transfection. Third, pH sensitivity: The amphiphilic peptide must be pH sensitive. Lysis activity can be controlled by the introduction of lysine, arginine and histidine residues into the hydrophilic face of JTS-1. Fourth, Lipid membrane interaction: The peptide must have a hydrophobic carboxyl terminal to permit interaction with lipid membranes, e.g., tyrosine substitution for tryptophan greatly reduces activity. Finally, Peptide chain length: The length must be greater than twelve residues in order to get stable helix formation and lipid membrane penetration and rupture.

Lytic Peptides, Analogs and Derivatives

In order to eliminate the use of adenovirus as an endosomal lysis agent, fusogenic or membrane disruptive peptides were designed which would increase the rate of delivery of nucleic acid from the endosome to the cell and ensure that higher concentrations of the endocytosed nucleic acid would be released and not degraded in the endosomes. In addition to pH sensitive liposomes (Liu & Haung,1990 Biochim Biophys Acta 1022:348–54), composed of phosphatidylsuccinylglycerol and phosphatidylethanolamine, lipophilic derivatives of GLFEALLELLESLWELLLEA SEQ ID NO:138 (JTS-1) and other lytic peptides were used. A number of fusogenic/lytic peptides have been previously described, including the amino terminal sequence of the vesicular stomatitis virus glycoprotein and the synthetic amphipathic peptide GALA. Ojcius et al., *TIBS*, 16:225–229 (1991); Doms et al., *Membrane Fusion*, pp. 313–335 (Marcel Dekker, Inc., N.Y. 1991); Subbarao et al., *Biochemistry*, 26:2964–2972 (1987).

Short synthetic peptides from the hemagglutinin $HA_2$ subunit of influenza have been studied with artificial lipid membranes. Wharton et al., *J. Gen. Virol.*, 69:1847–1857 (1988). These peptides give both membrane fusion and leakage of liposomal contents similar to whole hemagglutinin molecules. However, the rates are quite slower.

In order to increase the low efficiency rate by endosomal lysis with influenza peptides, new peptides were created. In creating these new peptides for endosomal lysis, four factors were considered: (1) the content and spacing of the hydrophilic and hydrophobic amino acid residues along the α-helix to direct organized oligomer association of the peptides after their insertion into the membrane; (2) covalent attachment of the peptide to a binding molecule and preclusion of oligomer formation and the necessary aggregation; (3) sufficient aggregation of several oligomeric structures necessary to achieve lysis; and (4) presence of hydrophilic carboxyl and amino side chain and terminal groups to create the pH sensitive endosomal processing.

It is well known that the distribution of the amino acid side chains along the peptide chain determines the secondary and tertiary structure of a protein. For membrane associating proteins, the amphipathic profile created by the hydrophobic and hydrophilic residues is a principal determinant of the function of the protein. Analysis of the region of the influenza hemagglutinin responsible for fusion of the viral envelope with the plasma membrane of cells reveals that a large hydrophobic surface is formed when the protein becomes α-helical.

In the present invention, a number of lytic peptides have been designed and tested for endosomal lytic activity. In order for these peptides to be functional, they must have the following parameters. These peptides are amphipathic membrane associating peptides. These amphipathic peptides were designed as an α-helix, containing a sequence of amino acids such that the side chains are distributed so that the peptide has a hydrophobic and hydrophilic side. The hydrophobic side contains highly apolar amino acid side chains, while the hydrophilic side contains an extensive number of glutamic acids.

In general, the amphipathic membrane associating peptides usually contain 21 amino acids or fewer. The design criteria requires that the amino acids have a high probability of forming amphiphilic species. This can be exhibited in the secondary structure of the membrane associating peptides, i.e., helices, turns, bends, loops, β-sheets, and their oligomeric aggregates and other super secondary structures defined in the literature, e.g., helix-turn-helix. In addition, the amino acids should have a high probability of being found in an α-helix and a low probability of forming a β-sheet or turn structure. Leucine, lysine and glutamate are appropriate amino acids for such characteristics. For example, lysine positioned on the lateral face of the α-helix and glutamate residues opposite leucine provide optimal charge distribution for lipid interaction. Furthermore, lysines and glutamates can be positioned to take advantage of potential helix stabilization. Helix dipole stabilization is optimized by removing the charge at the $NH_2$ and COOH-termini so $NH_2$ termini and COOH-terminal amides are useful. Such probabilities can be determined from secondary structural predictions or analogous methods to optimize secondary structural design. Unnatural amino acid which have been described for their propensity to induce helix structures in peptides are also used.

The hydrophobic or lipophilic face has a great effect on lipid-peptide interactions. Thus, the lipophilic face is modeled after peptides known to interact with lipids. Hydrophobic and lipid interactive residues (Ala, Leu, Met, Val, Phe, Trp, Tyr, Cys, Pro) when substituted on the lipophilic face either singularly or collectively promote a similar membrane associating effect. Similarly, an acid group and/or hydrophilic group (Glu, Gln, His, Lys, Gly, Ser, Asp, Asn, Pro, Arg) can be placed on the hydrophilic face to achieve the objective. The lipophilic and hydrophilic faces can also contain residues which promote lipid interaction and/or induce endosomal lysis at acidic pH. Such an interaction is not limited to an α-helix promoting residue since glycine and serine positioned on the hydrophilic face have been shown to favorably influence activity as seen with the examples below.

One in particular, the JTS-1 peptide, GLFEALLELLESLWELLLEA, SEQ ID NO:138 has a hydrophobic face which contains only strongly apolar amino acids, while the hydrophilic face is dominated by negatively charged glutamic acid residues at physiological pH values. At the amino terminus end, the JTS-1 peptide uses the Gly-Leu-Phe sequence at amino acid positions 1-2-3, respectively, as a fusogenic or membrane disruptive sequence. For increased pH sensitivity Glu is added at amino acid position 4. In addition, at positions 12–15, Ser-Leu-Trp-Glu is used as a lipid binding site. The remaining sequences are arranged to provide the hydrophobic and hydrophilic face of apoE-3. Amino acids 16, 9, 2, 13, 6, 17, 10, 3, 14, 7 and 18 form the hydrophobic face. Amino acids 5, 12, 1, 8, 15, 4 and 11 form the hydrophilic face.

The following JTS peptide was characterized for lytic activity: apoE-3 GLFEALLELLESLWELLLEA SEQ ID NO:138.

In addition to the above, n-acyl tetrapeptides with fusogenic or membrane destabilizing activity can be constructed. The structure of these is set forth in Smith et al., U.S. patent application Ser. No. 08/484,777, filed Dec. 18, 1995, incorporated herein by reference in its entirety including any drawings. The tetrapeptide sequence when substituted with the appropriate amino acids as discussed above are capable of interacting with lipid bilayers and thereby destabilizing. The acyl chain can be lengthened or shortened depending on structure/function requirements.

Furthermore, shorter α-helical peptides were also synthesized with the above design motifs in mind to retain the lytic properties as discussed above. Furthermore, a COOH-terminal amide is used to provide helix-dipole optimization. When in an α-helical structure the hydrophobic face appears at positions 4, 7, 3, and 10.

To provide the Gly-Leu-Phe fusogenic or membrane disruption activity to the above-mentioned α-helical peptide the peptide was lengthened to an 11-mer. Adding the additional amino acid to form the following peptide, Suc-GLFKLLEEWLE, SEQ ID NO:139 allowed the activity of the three glutamic acids to be retained. In addition, the peptide was succinylated at the amino terminus to afford an i to i+4 salt bridge with lysine which is designed to stabilize the helix.

Additional detailed descriptions of other lysis agents are provided in Smith et al., U.S. patent application Ser. No. 08/484,777, filed Dec. 18, 1995, incorporated herein by reference in its entirety including any drawings.

The term "surface ligand" as used herein refers to a chemical compound or structure which will bind to a surface receptor of a cell. The term "cell surface receptor" as used herein refers to a specific chemical grouping on the surface of a cell to which the ligand can attach. Cell surface receptors can be specific for a particular cell, i.e., found predominantly in one cell rather than in another type of cell (e.g., LDL and asialoglycoprotein receptors are specific for hepatocytes). The receptor facilitates the internalization of the ligand and attached molecules. A cell surface receptor includes, but is not limited to, a folate receptor, biotin receptor, lipoic acid receptor, low-density lipoprotein receptor, asialoglycoprotein receptor, insulin-like growth factor type II/cation-independent mannose-6-phosphate receptor, calcitonin gene-related peptide receptor, insulin-like growth factor I receptor, nicotinic acetylcholine receptor, hepatocyte growth factor receptor, endothelin receptor, bile acid receptor, bone morphogenetic protein receptor, cartilage induction factor receptor or glycosylphosphatidylinositol (GPI)-anchored proteins (e.g., β-andrenargic receptor, T-cell activating protein, Thy-1 protein, GPI-anchored 5' nucleotidase). These are nonlimiting examples.

A receptor is a molecule to which a ligand binds specifically and with relatively high affinity. It is usually a protein or a glycoprotein, but may also be a glycolipid, a lipidpolysaccharide, a glycosaminoglycan or a glycocalyx. For purposes of this invention, epitopes to which an antibody or its fragments binds is construed as a receptor since the antigen:antibody complex undergoes endocytosis. Furthermore, surface ligand includes anything which is capable of entering the cell through cytosis (e.g., endocytosis, potocytosis, pinocytosis).

As used herein, the term "ligand" refers to a chemical compound or structure which will bind to a receptor. This includes but is not limited to ligands such as asialoorosomucoid, asialoglycoprotein, folate, lipoic acid, biotin, as well as those compounds listed in PCT publication WO 93/18759, hereby incorporated by reference including all drawings, sketches or diagrams.

One skilled in the art will readily recognize that the ligand chosen will depend on which receptor is being bound. Since different types of cells have different receptors, this provides a method of targeting nucleic acid to specific cell types, depending on which cell surface ligand is used. Thus, the preferred cell surface ligand may depend on the targeted cell type.

The term "nuclear ligand" as used herein refers to a ligand which will bind a nuclear receptor. The term "nuclear receptor" as used herein refers to a chemical grouping on the nuclear membrane which will bind a specific ligand and help transport the ligand through the nuclear membrane. Nuclear receptors can be, but are not limited to, those receptors which bind nuclear localization sequences. Nonlimiting examples of nuclear ligands include those disclosed in PCT publication WO 93/18759, hereby incorporated by reference including all drawings, sketches, diagrams and illustrations.

As noted above, the surface ligand, the nuclear ligand and/or the lysis agent can be associated directly to the lipohilic peptide binding molecule or can be associated with the lipohilic peptide binding molecule via a spacer. Such as those described in Smith et al., supra, incorporated herein.

The macromolecule, as noted above, may be nucleic acid, such as DNA or RNA. The lipid moiety may be linked to the N-terminus of said delivery peptide and the delivery peptide may be non-covalently bound to said macromolecule. The macromolecule may be complexed with more than one lipophilic peptides, for example, with two, three, four, or five lipophilic peptides. The functional characteristics described above (i.e., condensation, lysis, nuclear targeting, etc.)can be separately performed from different peptide-macromolecule complexes. The delivery peptide may comprise a compound selected from the group consisting of: (1) apoE-3$^{129-169}$; (2) apoE-3$^{139-169}$; and (3) apoE-3$^{129-169Q142}$ as described in Mims et al., *Jour. Biol. Chem.* 269, 20539–20547.

In another aspect, the invention features a method of using a complex described above for delivering said macromolecule to a cell comprising the step of contacting said cell with said complex for a time sufficient to permit incorporation of said complex into said cell, wherein said macromolecule is delivered in a physiologically sufficient amount.

In preferred embodiments, the method also involves contacting said complex with a biological detergent capable of solubilizing and/or enmeshing said macromolecule. The term "enmeshed" as used herein refers to the covering, complexing or association of the delivery peptide with a nucleic acid macromolecule resulting in the condensation of the peptide-macromolecule complex. The detergentmay be selected from the group consisting of: CHAPS (N,N-dimethyl-N-(3-sulfopropyl)-3-[[3α,5β,7α,12α)-3,7,12-trihydroxy-24-oxocholan-24-yl]amino]-1-propanaminium hydroxide inner salt), 1-O-octyl-D-glucoside and other zwitterionic and neutral detergents except sodium cholate. The detergent preferably is present at a final concentration which is below the critical micelle concentration (cmc)of the detergent. The term "critical micelle concentration" refers to that concentration of detergent below which formation of micellar structures is promoted. In addition, the detergent preferably has a dilution ratio with said macromolecule sufficient to reduce the concentration of said detergent below its critical micelle concentration.

In another aspect, the invention features a cell transformed with a complex described above. As used herein "transformation" or "transformed" is a mechanism of gene transfer which involves the uptake of nucleic acid by a cell or organism. It is a process or mechanism of inducing transient or permanent changes in the characteristics (expressed phenotype) of a cell. Such changes are by a mechanism of gene transfer whereby DNA or RNA is introduced into a cell in a form where it expresses a specific gene product or alters the expression or effect of endogenous gene products. Following entry into the cell, the transforming nucleic acid may recombine with that of the host. Such transformation is considered stable transformation in that the introduction of gene(s) into the chromosome of the targeted cell where it integrates and becomes a permanent component of the genetic material in that cell. Gene expression after stable transformation can permanently alter the characteristics of the cell leading to stable transformation. In addition, the transforming nucleic acid may exist independently as a plasmid or a temperate phage, or by episomes. An episomal transformation is a variant of stable transformation in which the introduced gene is not incorporated in the host cell chromosomes but rather remains in a transcriptionally active state as an extrachromosomal element.

Transformation can be performed by in vivo techniques as described below, or by ex vivo techniques in which cells are cotransfected with a peptide-macromolecule complex containing nucleic acid and also containing a selectable marker. This selectable marker is used to select those cells which have become transformed. It is well known to those skilled in the art the type of selectable markers to be used with transformation studies.

The transformed cells can produce a variety of compounds selected from proteins, polypeptides or RNA, including hormones, growth factors, enzymes, clotting factors, apolipoproteins, receptors, drugs, tumor antigens, viral antigens, parasitic antigens, and bacterial antigens. Other examples can be found above in the discussion of nucleic acid. The product expressed by the transformed cell depends on the nucleic acid used. The above are only examples and are not meant to be limiting.

These methods of use would include the steps of contacting a cell with a peptide-macromolecule complex as described above for a sufficient time to transform the cell. Cell types of interest can include, but are not limited to, liver, muscle, lung, endothelium, bone, blood, joints and skin.

Other features and advantages of the invention will be apparent from the following detailed description of the invention in conjunction with the accompanying drawings and from the claims.

Figure 1:
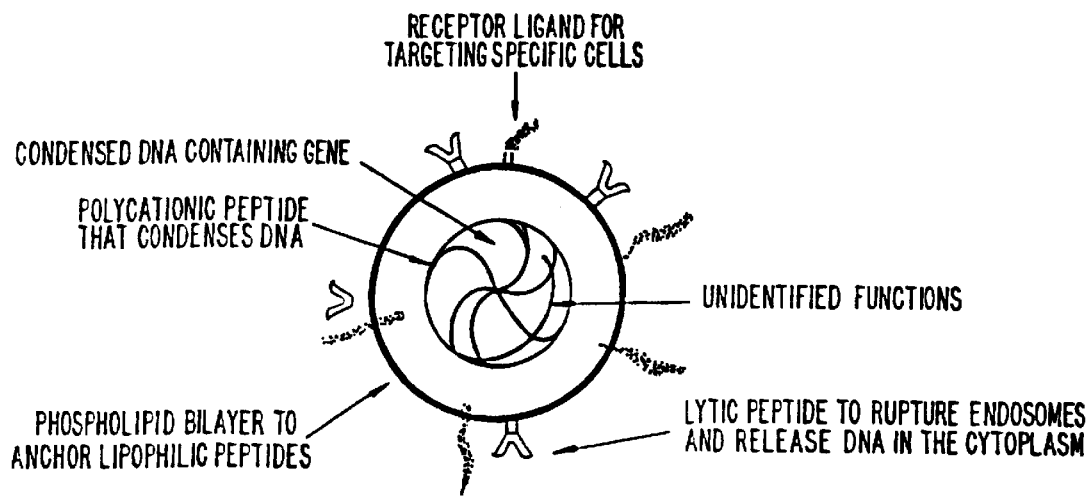
FIG. 1 represents a schematic drawing illustrating the various features of the current invention.
Figure 2:
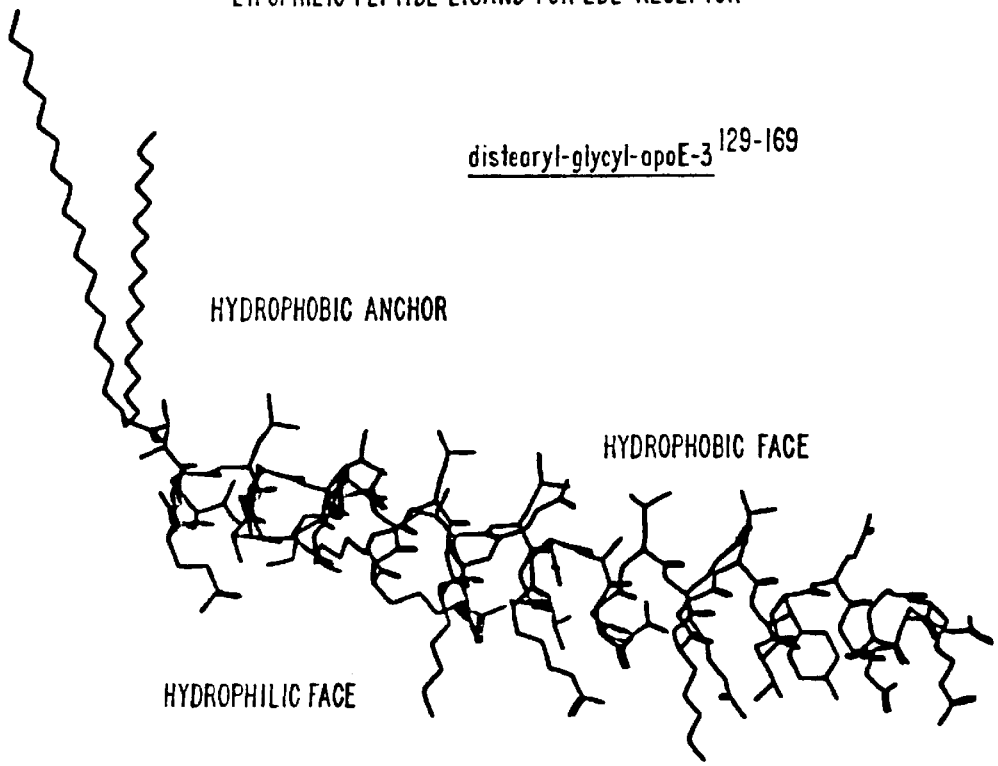
FIG. 2 represents the derivatived lipophilic peptide, distearyl-glycyl-apoE-3$^{129-169}$, illustrating the lipophilic anchor and amphipathic faces.
Figure 3:
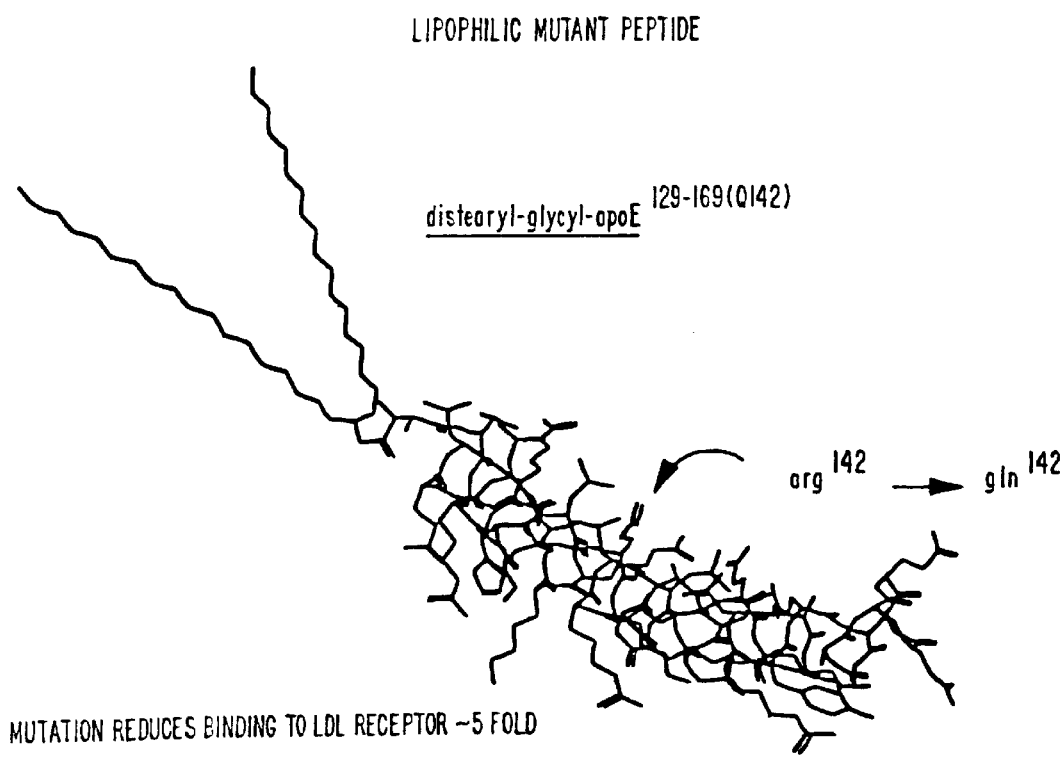
FIG. 3 represents the mutated derivatived lipophilic peptide, distearyl-glycyl-apoE-3$^{129-169(Q142)}$, illustrating the substituted amino acid (from arg to gln) at residue 142.
Figure 4:
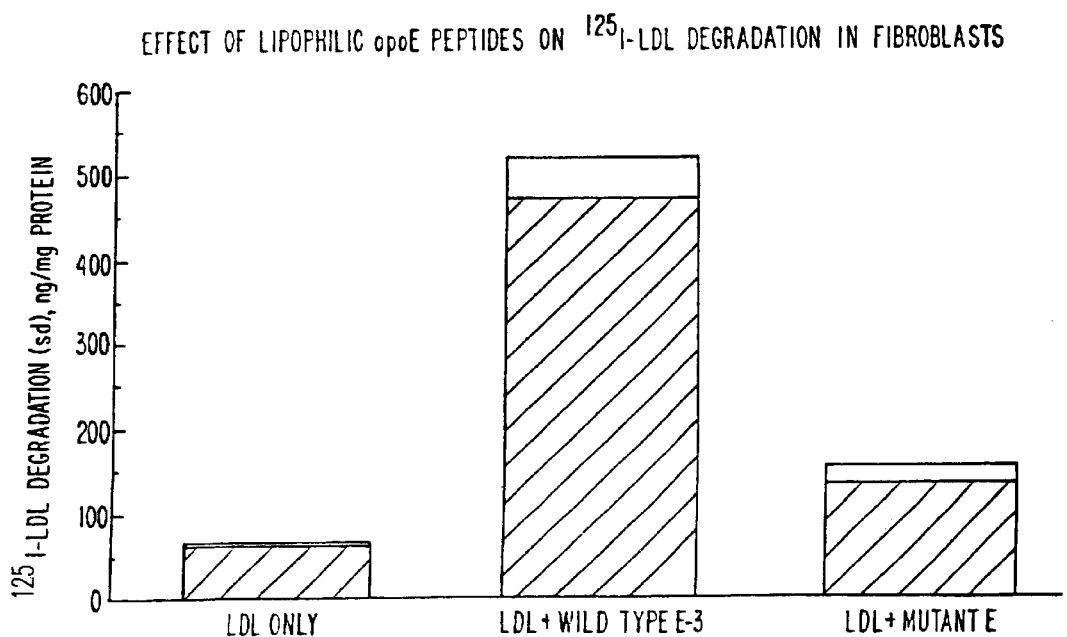
FIG. 4 illustrates the ability of labeled LDL to be cytosed and subsequently degraded when complexed with the derivatived lipophilic peptide, distearyl-glycyl-apoE-3$^{129-169}$. The mutated derivatived lipophilic peptide, distearyl-glycyl-apoE-3$^{129-169(Q142)}$ undergoes significantly less cytosis and degradation (cf. Mims et al.,op. cit).
Figure 5:
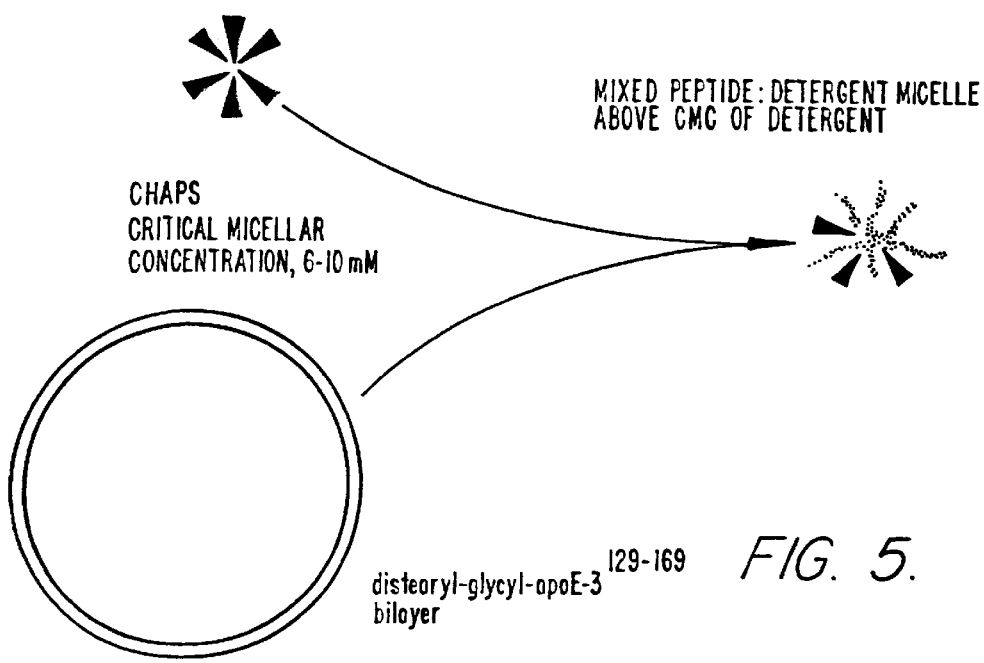
FIG. 5 illustrates the solubilization of the lipophilic peptide with the detergent CHAPS.
Figure 6:
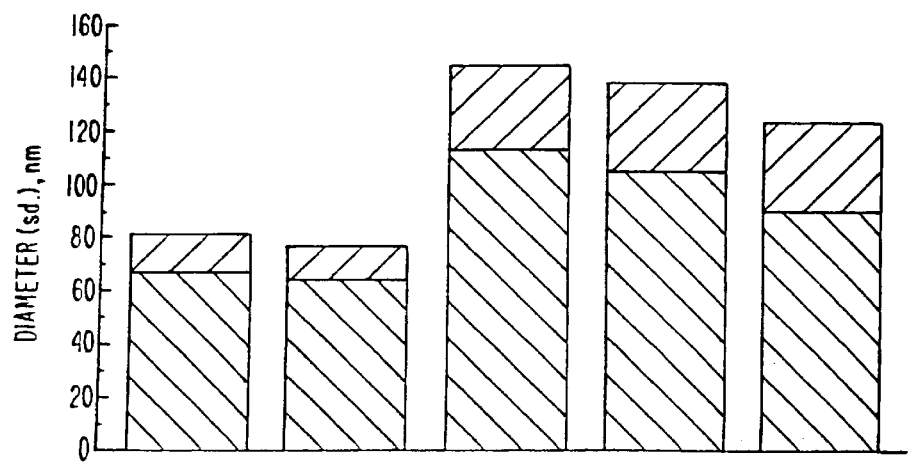
FIG. 6 illustrates the effect of various CHAPS concentrations on the size of condensed peptide-macromolecule complexes. Peptide-macromolecule complexes mixed with CHAPS below the critical micelle concentration of 5 mM show significant reduction in size (measured in diameter of the complex) compared to those complexes whose concentration of CHAPS was $\geq$5 mM.
Figure 7:
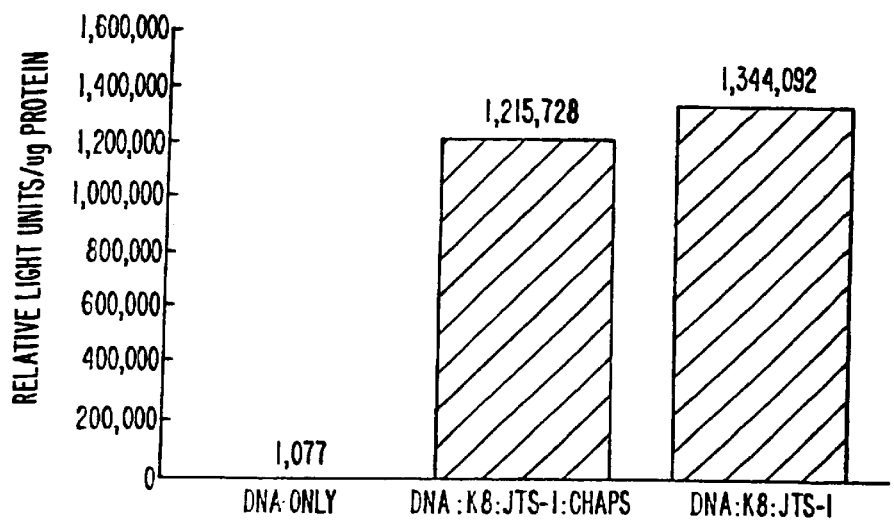
FIG. 7 illustrates that CHAPS concentrations have no significant effect on the ability of peptide-macromolecule complexes to transfect cells. Both peptide-macromolecule complexes alone and those complexed with the detergent expressed a foreign protein transfected into cells as measured by the relative light units given off from the expressed proteins.
Figure 8:
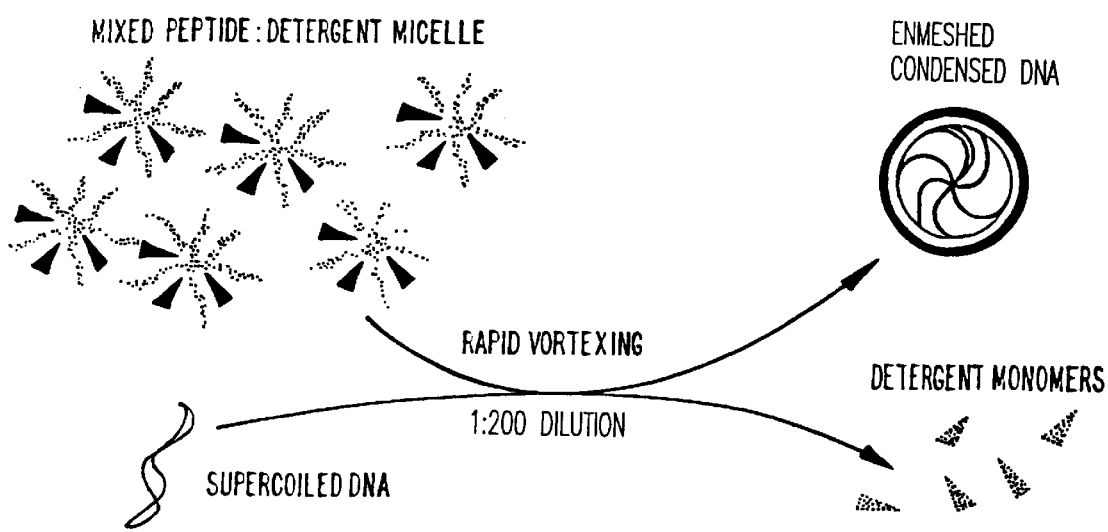
FIG. 8 illustrates the method of producing the peptide-macromolecular complex. Diluting the CHAPS concentration below its critical micelle concentration of 5 mM results in the unexpected and surprising result of enmeshment and condensation of nucleic acid with the solubilized lipophilic peptide producing a peptide-macromolecular complex of reduced diameter.
Figure 9:
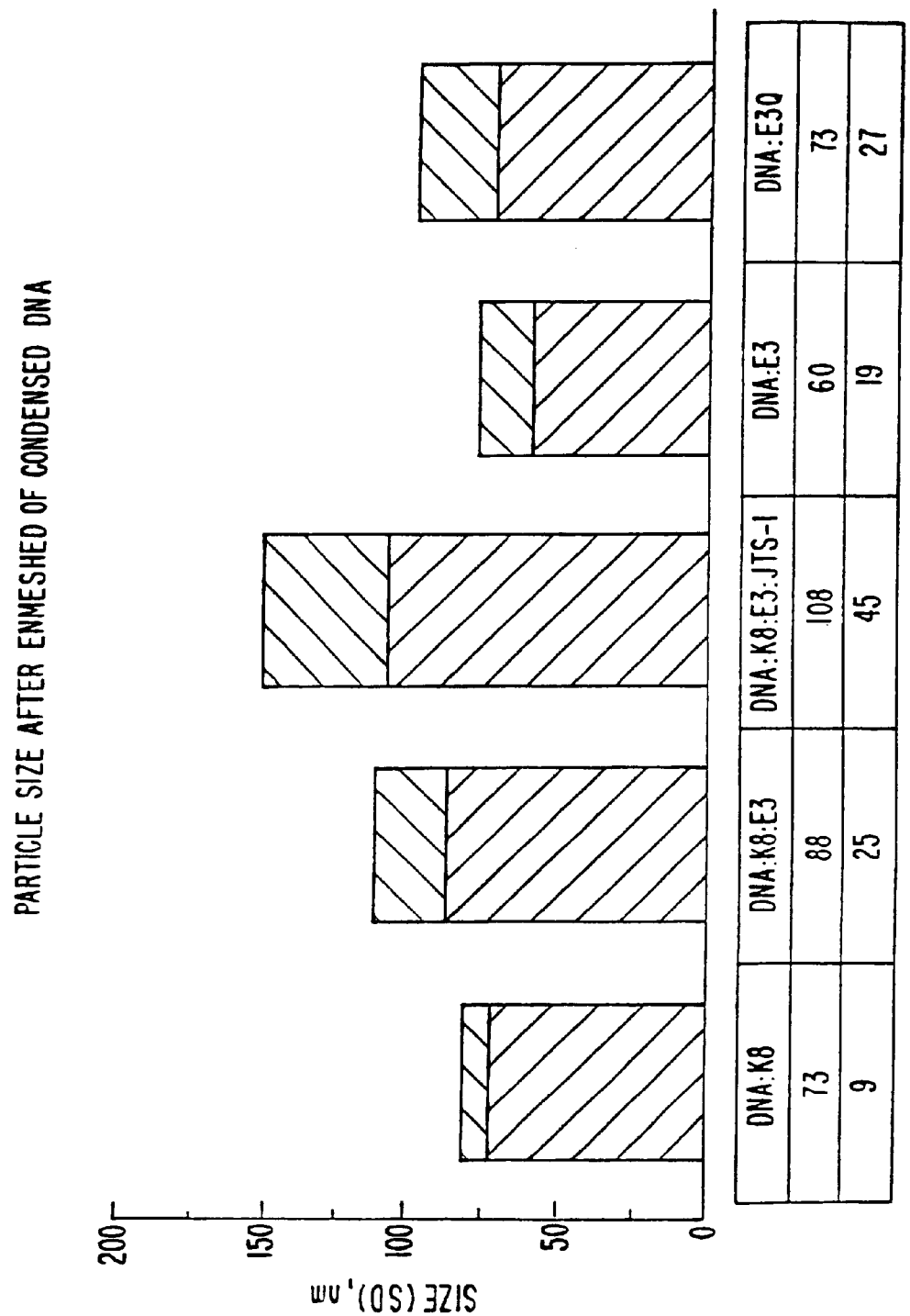
FIG. 9 illustrates the comparative sizes of various peptide complexes. Derivatived lipophilic peptide, distearyl-glycyl-apoE-3$^{129-169}$ (column 4; l. to r.) shows the greatest reduction in diameter after condensation.
Figure 10:
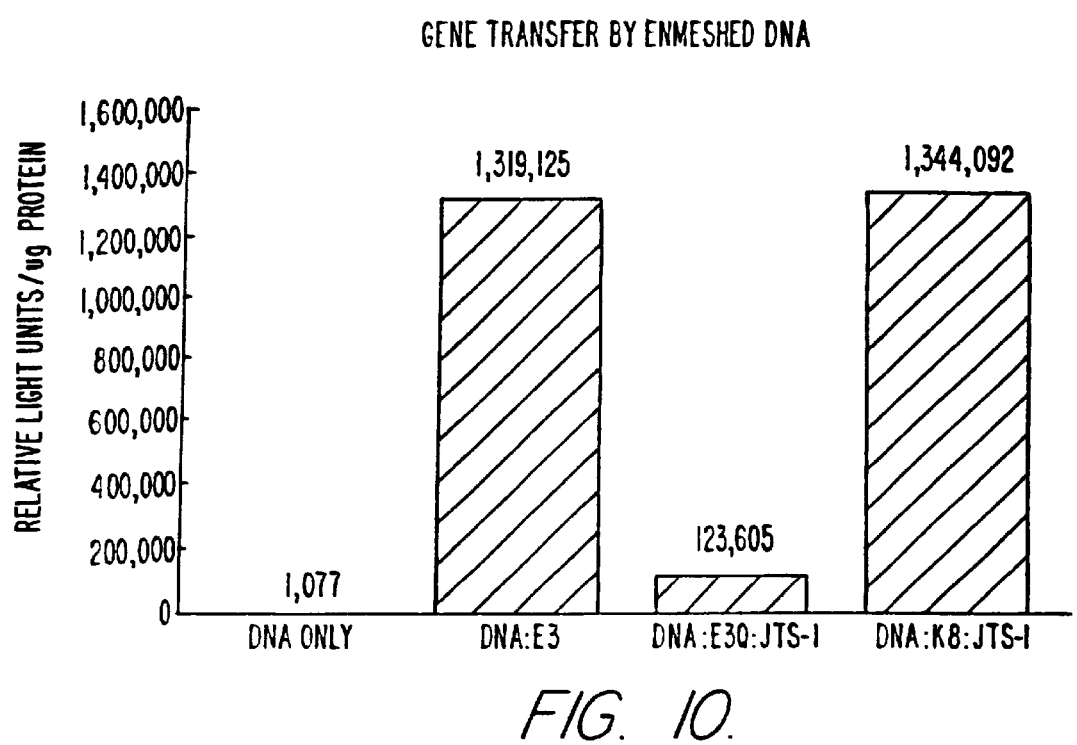
FIG. 10 illustrates the transfection ability of various peptide-macromolecule complexes. No significant transfection difference exists between the derivatived lipophilic peptide, distearyl-glycyl-apoE-3$^{129-169}$ and the galactosialated-lytic lipophilic peptide K8:JTS-1. However, the mutated derivatived lipophilic peptide, distearyl-glycyl-apoE-3$^{129-169(Q142)}$ shows significantly less transfection. Presumably due to the inability of the mutated peptide to undergo receptor mediated endocytosis and subsequent expression of the delivered nucleic acid.

The drawings are not necessarily to scale. Certain features of the invention may be exaggerated in scale or shown in schematic form in the interest of clarity and conciseness. In addition, the drawings of PCT publication WO 93/18759 are hereby incorporated by reference.

DETAILED DESCRIPTION OF THE INVENTION

The following are specific examples of preferred embodiments of the present invention using peptide-macromolecule complexes with lipophilic peptides for delivery of nucleic acid and other macromolecules to a cell. These examples are offered by way of illustration and are not intended to limit the invention in any manner.

These examples demonstrate how specific lipophilic peptides stabilize and condense the nucleic acid for cell delivery. Furthermore, these examples demonstrate how surface and nuclear ligands can be used with a delivery peptide to target nucleic acid into the cellular interior and/or the cell nucleus. Such targeted delivery is enhanced by use of the lysis agent and lipophilic peptides. These examples include in vivo and in vitro techniques, various cellular or animal models and how nucleic acid can be inserted into cells.

The utility of such peptide-macromolecule complexes is noted herein and is amplified upon in the PCT publication WO 93/18759, by Woo et al., entitled "A DNA Carrier System and Method of Use," hereby incorporated by reference. Below are provided examples of specific peptide-macromolecule complexes that can be used to provide certain functionalities to the associated nucleic acid in the peptide-macromolecule complex, and thus within a transformed cell or animal containing such associated nucleic acid. Those in the art will recognize that specific moieties of the peptide-macromolecule complex can be identified as that containing the functional region providing the desirable properties of the peptide-macromolecule complex. Such regions can be readily minimized using routine deletion, mutation, or modification techniques or their equivalent.

The complexes or carrier systems of the present invention enhance delivery of nucleic acid into the cell preferably by using synthetic lysis and nucleic acid lipophilic peptide binding molecules. In particular, the specific lysis agents are useful in disrupting the endosome thereby allowing the nucleic acid to avoid lysosomal degradation. The specific lipophilic peptide binding molecules are useful in delivering to the cell stabilized and condensed nucleic acid. In addition, these specific lipophilic peptides are useful in delivering stabilized and condensed nucleic acid into the nucleus of the cell. These carriers can be used to treat diseases by enhancing delivery of specific nucleic acid to the appropriately targeted cells. These carriers can also be used to create transformed cells, as well as transgenic animals for assessing human disease in an animal model.

The present invention also takes advantage of DNA lipophilic peptides in order to increase DNA stability and DNA delivery to cells. In particular, the present invention features use of nucleic acid carriers with nucleic acid non-covalently bound to peptides capable of condensing the nucleic acid. These lipophilic peptides provide smaller, or condensed, and more stable nucleic acid particles for delivery, thereby enhancing the transfection rates of the nucleic acid into the cell and into the nucleus.

By taking advantage of the characteristics of both the lysis agents and lipophilic peptides, the present invention enhances delivery of nucleic acid by the nucleic acid carrier system. These components can be used alone, together or with other components of the nucleic acid carrier described below and disclosed in PCT publication WO 93/18759, Woo et al., entitled "A DNA Carrier System and Method of Use," the whole of which (including drawings) is hereby incorporated by reference. The carrier system, together with the lysis and lipophilic peptides, enhances the delivery of nucleic acid to specific cells by enhancing the release of stable, condensed nucleic acid from the endosome into the cellular interior.

In addition to the nucleic acid, lipophilic peptides and the nucleic acid binding complex containing the lysis agent, the present invention also features various nucleic acid binding complexes which contain a surface ligand and a nuclear ligand as well. The surface ligands are capable of binding to a cell surface receptor and entering a cell through cytosis (e.g., endocytosis, potocytosis, pinocytosis). By using surface ligands specific to certain cells, nucleic acid can be delivered using the peptide-macromolecule complexes directly to the desired tissue. The nuclear ligands are capable of recognizing and transporting nucleic acid through the nuclear membrane to the nucleus of a cell. Such nuclear ligands help enhance the lipophilic peptides' ability to target nucleic acid to the nucleus.

Furthermore, the present invention features peptides which have been derivatized by modification of their N termini through acylation with either palmitic acid or the N, N,-distearyl derivative of glycine. Such modifications create lipophilicity in the treated peptide by increasing the $K_d$ value of the new compound when it becomes associated with a lipid; thus, the derivatization effectively increases the affinity of the peptide for lipid surfaces to which it is originally bound and decreases the propensity of the bound lipophilic peptide for promiscuous transfer to other lipid surfaces. Therefore, once the derivatized peptide is complexed in a nucleic acid delivery complex, the palmitic acids or the N, N,-distearyl modification will anchor the peptide and prevent its transfer to other non-targeted lipid surfaces with which it may come into contact during in vivo circulation. Consequently, an additional advantage of the present invention is the ability of the lipophilic peptide binding moiety to remain circulating in vivo for lengthy transmission times until it reaches its specified target. This is possible because the derivatization of the peptide prevents the inadvertent loss of either the associated target ligand or nucleic acid through non-specific adsorption to erythrocytes, vascular cell surfaces, or lipid-associated plasma proteins that it may come into contact with during its circulation throughout the body. This improved feature of the invention promotes greater efficiency in the transfection of targeted cells and decreased dosages during administration thus, resulting in fewer potential deleterious side-effects. Should a shorter lived complex be desired, a twelve carbon anchoring moiety could be used. This is merely an illustrative and not a limiting example. The $K_d$ is determined thermodynamically by the hydrophobicity of the lipophilic group, i.e., the alkyl or fatty acyl residues.

An additional advantageous feature of the present invention is that the palmitic acid or N, N,-distearyl modification increases the α-helicity of the treated peptide in the presence of lipid. This is an additional beneficial feature because it has been shown that the N-terminal domain of the peptide mediates binding of the peptide to its target receptor via a fourth-helix bundle. This helical domain of the peptide shows a 500-fold decrease in binding capacity for its target receptor when the peptide modification has been removed or delipitated. Therefore, the effect of the lipid modification on the α-helicity of the modified peptide results in its unfolding without disruption of the α-helices, thereby producing a receptor-active conformation and appropriate binding to targeted cells.

The abilities of the above carriers to deliver nucleic acid to specific cells and to the nucleus also allows transgenic animal models to be used for the dissection of molecular carcinogenesis and disease, assessing potential chemical and physical carcinogens and tumor promoters, exploring model therapeutic avenues as well as livestock agricultural purposes. Furthermore, the above peptide-macromolecule complex advantages allow methods for administration and treatment of various diseases. In addition, the above peptide-macromolecule complexes can be used to transform cells to produce particular proteins, polypeptides, and/or RNA. Likewise, the above peptide-macromolecule complexes can be used in vitro with tissue culture cells. In vitro uses allow the role of various nucleic acids to be studied by targeting specific expression into specifically targeted tissue culture cells.

The present invention also encompasses a transgenic animal whose cells contain the nucleic acid referenced above delivered via the peptide-macromolecule complex. These cells include germ or somatic cells. Transgenic animal models can be used for dissection of molecular carcinogenesis and disease, assessing potential chemical and physical carcinogens and tumor promoters, exploring model therapeutic avenues and livestock agricultural purposes.

The methods of use also include a method of treating humans, which is another aspect of the present invention. The method of treatment includes the steps of administering the nucleic acid carriers as described above so as to deliver a desired nucleic acid to a cell or tissue for the purposes of expression of the nucleic acid by the cell or tissue. Cell or tissue types of interest can include, but are not limited to, liver, muscle, lung, endothelium, joints, skin, bone and blood.

The methods of treatment or use include methods for delivering nucleic acid into a hepatocyte by contacting a hepatocyte with the above referenced nucleic acid carriers. The surface ligand used with the nucleic acid carrier is one specific for recognition by hepatocyte receptors. In particular, the asialoorosomucoid protein is used as a cell surface ligand, apoE-3, or a derivative as a lipophilic peptide binding molecule and JTS-1 or a derivative as a lysis agent. Furthermore, these methods of use also include delivery of nucleic acids using a carrier with apoE-3 and no surface or nuclear ligands. The term "hepatocyte" as used herein refers to cells of the liver.

An aspect of the methods of treatment or use includes a method for delivering nucleic acid to muscle cells by contacting the muscle cell with one of the above referenced peptide-macromolecule complex. The surface ligand used is specific for receptors contained on the muscle cell. In particular, the surface ligand can be insulin-like growth factor-I. In addition, the lipophilic peptide binding molecule can be a apoE-3, or a derivative and the lysis agent can be JTS-1 or a derivative. In addition, exchangeable lipids present in plasma, whole blood, and uniquely associated with specific compartments of the body such as, but not restricted to, the pleural airways, the peritoneal cavity, the interstitial spaces of tumors and tissues can be included as additional components of the peptide-macromolecue complex so that the peptide-macromolecue complexes may differ both qualitatively and quantitatively depending upon what portion of the body they will be targeted. Furthermore, these methods of treatment or use also include delivery of nucleic acids using a carrier with apoE-3 and no surface or nuclear ligands. The term "muscle cell" as used herein refers to cells associated with striated muscle, smooth muscle or cardiac muscle.

Another aspect of the methods of treatment or use includes a method for delivering nucleic acid to bone-forming cells by contacting the bone-forming cell with the above referenced peptide-macromolecule complex. The surface ligand used with the peptide-macromolecule complex is specific for receptors associated with bone-forming cells. In particular, the surface ligands can include, but are not limited to, bone morphogenetic protein or cartilage induction factor. In addition, thelipophilic peptide binding molecule of the nucleic acid carrier can be apoE-3, or a derivative, and the lysis agent JTS-1 or a derivative thereof. Furthermore, these methods of treatment or use also include delivery of nucleic acids using a carrier with apoE-3 and no surface or nuclear ligands. As used herein the term "bone-forming cell" refers to those cells which promote bone growth. Nonlimiting examples include osteoblasts, stromal cells, inducible osteoprogenitor cells, determined osteoprogenitor cells, chondrocytes, as well as other cells capable of aiding bone formation.

Another related aspect of the methods of treatment or use includes a method for delivering nucleic acid to a cell using the above referenced peptide-macromolecule complex. The peptide-macromolecule complex uses folate as a ligand. In addition, the nucleic acid carrier can use JTS-1 or a derivative as a lysis agent, and apoE-3, or a derivative thereof as a lipophilic peptide binding molecule. This method targets cells which contain folate receptors, including, but not limited to, hepatocytes.

Still another related aspect of the methods of treatment or use includes a method for delivering nucleic acid to synovialcytes or macrophages using the above referenced peptide-macromolecule complex. The peptide-macromolecule complex uses a ligand recognized by synovialcytes and/or macrophages. In addition, the nucleic acid carrier can use JTS-1 or a derivative as a lysis agent, and apoE-3, or a derivative thereof as a lipophilic peptide binding molecule. Furthermore, this method of use also includes delivery of nucleic acids using a carrier with apoE-3 and no surface or nuclear ligands. The term "synoviacytes" refers to cells associated with the joints or with the fluid space of the joints.

In addition to the above methods, the method of use also includes delivery using a nuclear ligand binding complex as well. Such nuclear carriers would help direct the nucleic acid to the nucleus of the cell. Furthermore, the above methods of use also include nucleic acid carriers with thelipophilic peptide binding molecule and the lysis agent, or a plurality thereof.

The nucleic acid carriers of the above methods may be administered by various routes. The term "administration" or "administering" refers to the route of introduction of the nucleic acid carrier or carrier of the carrier into the body. Administration may be intravenous, intramuscular, topical, olfactory or oral. Administration can be directly to a target tissue or through systemic delivery. In particular, administration may be by direct injection to the cells. In another embodiment, administration may be intravenously, by hypospray or the use of PVP, an amorphous powder. Routes of administration include intramuscular, aerosol, oral, topical, systemic, olfactory, ocular, intraperitoneal and/or intratracheal.

Cell Transformation

One embodiment of the present invention includes cells transformed with nucleic acid associated with the peptide-macromolecule complexes described above. Once the cells are transformed, the cells will express the protein, polypeptide or RNA encoded for by the nucleic acid. Cells included, but are not limited to, liver, muscle and skin. This description is not intended to be limiting in any manner.

The nucleic acid which contains the genetic material of interest is positionally and sequentially oriented within the host or vectors such that the nucleic acid can be transcribed into RNA and, when necessary, be translated into proteins or polypeptides in the transformed cells. A variety of proteins and polypeptides can be expressed by the sequence in the nucleic acid cassette in the transformed cells. These products may function as intracellular or extracellular structural elements, ligands, hormones, neurotransmitters, growth regulating factors, apolipoproteins, enzymes, serum proteins, receptors, carriers for small molecular weight compounds, drugs, immunomodulators, oncogenes, tumor suppressors, toxins, tumor antigens, antigens, antisense inhibitors, triple strand forming inhibitors, ribozymes, or as a ligand recognizing specific structural determinants on cellular structures for the purpose of modifying their activity.

Transformation can be done either by in vivo or ex vivo techniques. One skilled in the art will be familiar with such techniques for transformation. Transformation by ex vivo techniques includes co-transfecting the cells with DNA containing a selectable marker. This selectable marker is used to select those cells which have become transformed. Selectable markers are well known to those who are skilled in the art.

For example, one approach to nucleic acid delivery for hepatic diseases is to remove hepatocytes from an affected individual, genetically alter them in vitro, and reimplant them into a receptive locus. The ex vivo approach includes the steps of harvesting hepatocytes, cultivating the hepatocytes, transducing or transfecting the hepatocytes, and introducing the transfected hepatocytes into the affected individual.

The hepatocytes may be obtained in a variety of ways. They may be taken from the individual who is to be later injected with the hepatocytes that have been transformed or they can be collected from other sources, transformed and then injected into the individual of interest.

Once the ex vivo hepatocyte is collected, it may be transformed by contacting the hepatocytes with media containing the nucleic acid carrier and maintaining the cultured hepatocytes in the media for sufficient time and under conditions appropriate for uptake and transformation of the hepatocytes. The hepatocytes may then be introduced into an orthotopic location (the body of the liver or the portal vasculature) or heterotopic locations by injection of cell suspensions into tissues. One skilled in the art will recognize that the cell suspension may contain: salts, buffers or nutrients to maintain viability of the cells; proteins to ensure cell stability; and factors to promote angiogenesis and growth of the implanted cells.

In an alternative method, harvested hepatocytes may be grown ex vivo on a matrix consisting of plastics, fibers or gelatinous materials which may be surgically implanted in an orthotopic or heterotopic location after transduction. This matrix may be impregnated with factors to promote angiogenesis and growth of the implanted cells. Cells can then be reimplanted. The above are only examples and are nonlimiting.

Administration

Administration as used herein refers to the route of introduction of the nucleic acid carriers into the body. Administration includes intravenous, intramuscular, systemic, subcutaneous, subdermal, topical, or oral methods of delivery. Administration can be directly to a target tissue or through systemic delivery.

In particular, the present invention can be used for administering nucleic acid for expression of specific nucleic acid sequence in cells. Routes of administration include intramuscular, aerosol, olfactory, oral, topical, systemic, ocular, intraperitoneal and/or intratracheal. A preferred method of administering nucleic acid carriers is by intravenous delivery. Another preferred method of administration is by direct injection into the cells.

Transfer of genes directly has been very effective. Experiments show that administration by direct injection of DNA into joints and thyroid tissue results in expression of the gene in the area of injection. Injection of plasmids containing IL-1 into the spaces of the joints results in expression of the gene for prolonged periods of time. The injected DNA appears to persist in an unintegrated extrachromosomal state. This means of transfer is one of the preferred embodiments.

In addition, another means to administer the nucleic acid carriers of the present invention is by using a dry powder form for inhalation. One compound which can be used is polyvinylpyrrolidone ("PVP"), an amorphous powder. PVP is a polyamide that forms complexes with a wide variety of substances and is chemically and physiologically inert. Specific examples of suitable PVP's are Plasdone-C®15, MW 10,000 and Plasdone-C®30, MW 50,000. Furthermore, administration may also be through an aerosol composition or liquid form into a nebulizer mist and thereby inhaled.

The special delivery route of any selected vector construct will depend on the particular use for the nucleic acid associated with the nucleic acid carrier. In general, a specific delivery program for each nucleic acid carrier used will focus on uptake with regard to the particular targeted tissue, followed by demonstration of efficacy. Uptake studies will include uptake assays to evaluate cellular uptake of the nucleic acid and expression of the specific nucleic acid of choice. Such assays will also determine the localization of the target nucleic acid after uptake, and establishing the requirements for maintenance of steady-state concentrations of expressed protein. Efficacy and cytotoxicity is then tested. Toxicity will not only include cell viability but also cell function.

Incorporated DNA into carriers, as described herein, which undergo endocytosis increases the range of cell types that will take up foreign genes from the extracellular space.

The chosen method of delivery should result in cytoplasmic accumulation and optimal dosing. The dosage will depend upon the disease and the route of administration but should be between 0.1–1000 mg/kg of body weight/day. This level is readily determinable by standard methods. It could be more or less depending on the optimal dosing. The duration of treatment will extend through the course of the disease symptoms, possibly continuously. The number of doses will depend upon disease delivery vehicle and efficacy data from clinical trials.

Establishment of therapeutic levels of DNA within the cell is dependent upon the rate of uptake and degradation. Decreasing the degree of degradation will prolong the intracellular half-life of the DNA.

Direct Delivery to the Liver

Nucleic acid carriers of the present invention can also be used in reversing or arresting the progression of disease involving the liver, such as liver cancer. One embodiment involves use of intravenous methods of administration to delivery nucleic acid encoding for a necessary molecule to treat disease in the liver. Nucleic acid carriers which express a necessary protein or RNA can be directly injected into the liver or blood supply so as to travel directly to the liver. Finally, a dry powder form, such as PVP discussed above, can be used to treat disease in the liver. The dry powder form is delivered by inhalation. These treatments can be used to control or suppress liver cancer or other liver diseases by expression of a particular protein encoded by the nucleic acid chosen.

One skilled in the art would readily appreciate that the present invention is well adapted to carry out the objects and obtain the ends and advantages mentioned, as well as those inherent therein. The peptide-macromolecule complexes along with the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

Direct DNA Delivery to Muscle

The muscular dystrophies are a group of diseases that result in abnormal muscle development, due to many different reasons. These diseases can be treated by using the direct delivery of genes with the nucleic acid carriers of the present invention resulting in the production of normal gene product. Delivery to the muscle using the present invention is done to present genes that produce various antigens for vaccines against a multitude of infections of both viral and parasitic origin. The detrimental effects caused by aging can also be treated using the nucleic acid delivery system described herein. Since the injection of the growth hormone protein promotes growth and proliferation of muscle tissue, the growth hormone gene can be delivered to muscle, resulting in both muscle growth and development, which is decreased during the later portions of the aging process. Genes expressing other growth related factors can be delivered, such as Insulin Like Growth Factor-1 (IGF-1). Furthermore, any number of different genes may be delivered by this method to the muscle tissue.

IGF-1 can be used to deliver DNA to muscle, since it undergoes uptake into cells by receptor-mediated endocytosis. This polypeptide is 70 amino acids in length and is a member of the growth promoting polypeptides structurally related to insulin. It is involved in the regulation of tissue growth and cellular differentiation affecting the proliferation and metabolic activities of a wide variety of cell types, since the polypeptide has receptors on many types of tissue. As a result, the nucleic acid carrier delivery system of the present invention utilizes IGF-1 as a ligand for tissue-specific nucleic acid delivery to muscle. The advantage of the IGF-1/nucleic acid delivery system is that the specificity and the efficiency of the delivery is greatly increased due to a great number of cells coming into contact with the ligand/nucleic acid complex with uptake through receptor-mediated endocytosis. Using the nucleic acid described above in the delivery systems of the present invention with the use of specific ligands for the delivery of nucleic acid to muscle cells provides treatment of diseases and abnormalities that affect muscle tissues.

In addition to the above, Factor IX can also be delivered to the muscle cells. DNA encoding Factor IX can be delivered using the nucleic acid carriers of the present invention. As a result, the nucleic acid carrier delivery system of the present invention utilizes nucleic acids encoding Factor IX to treat cells which are Factor IX deficient and are susceptible to disease and abnormalities due to such a deficiency. DNA encoding Factor IX can be coupled or associated with $K_8$ and apoE-3 as described above. The complex can then be delivered directly to muscle cells for expression. The preferred ratio of DNA to $K_8$ to apoE-3 is 1:3:1. Direct injection of the above complex is preferred. Use of the above nucleic acid delivery system of the present invention for the delivery of nucleic acid expressing Factor IX to muscle cells provides treatment of diseases and abnormalities that affect muscle tissues.

Direct DNA Delivery to Osteogenic Cells

There are many other problems that occur during the aging process, but one major problem is osteoporosis, which is the decrease in overall bone mass and strength. The direct nucleic acid delivery system of the present invention can be used to deliver genes to cells that promote bone growth. The osteoblasts are the main bone forming cell in the body, but there are other cells that are capable of aiding in bone formation. The stromal cells of the bone marrow are the source of stem cells for osteoblasts. The stromal cells differentiate into a population of cells known as Inducible Osteoprogenitor Cells (IOPC), which then under induction of growth factors, differentiate into Determined Osteoprogenitor Cells (DOPC). It is this population of cells that mature directly into bone producing cells. The IOPCs are also found in muscle and soft connective tissues. Another cell involved in the bone formation process is the cartilage-producing cell known as the chondrocyte.

The factor that has been identified to be involved in stimulating the IOPCs to differentiate is known as Bone Morphogenetic Protein (BMP). This 19,000 MW protein was first identified from demineralized bone. Another factor similar to BMP is Cartilage Induction Factor (CIF), which functions to stimulate IOPCs to differentiate also, starting the pathway of cartilage formation, cartilage calcification, vascular invasion, resorption of calcified cartilage, and finally induction of new bone formation. Cartilage Induction Factor has been identified as being homologous to Transforming Growth Factor β.

Since osteoblasts are involved in bone production, genes that enhance osteoblast activity can be delivered directly to these cells. Genes can also be delivered to the IOPCs and the chondrocytes, which can differentiate into osteoblasts, leading to bone formation. BMP and CIF are the ligands that can be used to deliver genes to these cells. Genes delivered to these cells promote bone formation or the proliferation of osteoblasts. The polypeptide, IGF-1 stimulates growth in hypophysectomized rats which could be due to specific uptake of the polypeptide by osteoblasts or by the interaction of the polypeptide with chondrocytes, which result in the formation of osteoblasts. Other specific bone cell and growth factors can be used through the interaction with various cells involved in bone formation to promote osteogenesis.

Nonlimiting examples of genes expressing the following growth factors which can be delivered to these cell types are Insulin, Insulin-Like Growth Factor-1, Insulin-Like Growth Factor-2, Epidermal Growth Factor, Transforming Growth Factor-α, Transforming Growth Factor-β, Platelet Derived Growth Factor, Acidic Fibroblast Growth Factor, Basic Fibroblast Growth Factor, Bone Derived Growth Factors, Bone Morphogenetic Protein, Cartilage Induction Factor, Estradiol, and Growth Hormone. All of these factors have a positive effect on the proliferation of osteoblasts, the related stem cells, and chondrocytes. As a result, BMP or CIF can be used as conjugates to deliver genes that express these growth factors to the target cells by the intravenous injection of the nucleic acid/Protein complexes of the present invention. Using the nucleic acid described above in the delivery systems of the present invention with the use of specific ligands for the delivery of nucleic acid to bone cells provides treatment of diseases and abnormalities that affect bone tissues.

Direct DNA Delivery to the Synovialcytes

The inflammatory attack on joints in animal models and human diseases may be mediated, in part, by secretion of cytokines such as IL-1 and IL-6 which stimulate the local inflammatory response. The inflammatory reaction may be modified by local secretion of soluble fragments of the receptors for these ligands. The complex between the ligand and the soluble receptor prevents the ligand from binding to the receptor which is normally resident on the surface of cells, thus preventing the stimulation of the inflammatory effect. Therapy consists of the construction of a vector containing the soluble form of receptors for appropriate cytokines (for example, IL-1), together with promoters capable of inducing high level expression in structures of the joint and a formulation which enables efficient uptake of this vector. This DNA is then used with the DNA carriers of the present invention. This DNA is injected into affected joints where the secretion of an inhibitor for IL-1 such as a soluble IL-1 receptor or natural IL-I inhibitor modifies the local inflammatory response and resulting arthritis.

This method is useful in treating episodes of arthritis which characterize many "autoimmune" or "collagen vascular" diseases. This method can also prevent disabling injury of large joints by inflammatory arthritis.

In addition to the above, the present invention can also be used with the following method. Current therapy for severe arthritis involves the administration of pharmacological agents including steroids to depress the inflammatory response. Steroids can be administered systemically or locally by direct injection into the joint space.

Steroids normally function by binding to receptors within the cytoplasm of cells. Formation of the steroid-receptor complex changes the structure of the receptor so that it becomes capable of translocating to the nucleus and binding to specific sequences within the genome of the cell and altering the expression of specific genes. Genetic modifications of the steroid receptor can be made which enable this receptor to bind naturally occurring steroids with higher affinity, or bind non-natural, synthetic steroids, such as RU486. Other modifications can be made to create steroid receptor which is "constitutively active" meaning that it is capable of binding to DNA and regulating gene expression in the absence of steroid in the same way that the natural steroid receptor regulates gene expression after treatment with natural or synthetic steroids.

Of particular importance is the effect of glucocorticoid steroids such as cortisone, hydrocortisone, prednisone, or dexamethasone which are the most important drugs available for the treatment of arthritis. One approach to treating arthritis is to introduce a vector in which the nucleic acid cassette expresses a genetically modified steroid receptor into cells of the joint, e.g., a genetically modified steroid receptor which mimics the effect of glucocorticoids but does not require the presence of glucocorticoids for effect. This is termed the glucocortico-mimetic receptor. This is achieved by expression of a constitutively active steroid receptor within cells of the joint which contains the DNA binding domain of a glucocorticoid receptor. This induces the therapeutic effects of steroids without the systemic toxicity of these drugs. Alternatively, steroid receptors which have a higher affinity for natural or synthetic glucocorticoids, such as RU486, can be introduced into the joint. These receptors exert an increased anti-inflammatory effect when stimulated by non-toxic concentrations of steroids or lower doses of pharmaco-logically administered steroids. Alternatively, constitution of a steroid receptor which is activated by a novel, normally-inert steroid enables the use of drugs which would affect only cells taking up this receptor. These strategies obtain a therapeutic effect from steroids on arthritis without the profound systemic complications associated with these drugs. Of particular importance is the ability to target these genes differentially to specific cell types (for example synovial cells versus lymphocytes) to affect the activity of these cells.

As described in U.S. Pat. No. 5,364,791 to Vegeto, et al., entitled "Progesterone Receptor Having C Terminal Hormone Binding Domain Truncations," and U.S. application, Ser. No. 07/939,246, entitled "Mutated Steroid Hormone Receptors, Methods for Their Use and Molecular Switch for Gene Therapy," Vegeto, et al., filed Sep. 2, 1992, both hereby incorporated by reference (including drawings), genetically modified receptors, such as the glucocorticomimetic receptor, can be used to create novel steroid receptors including those with glucocortico-mimetic activity. The steroid receptor family of gene regulatory proteins is an ideal set of such molecules. These proteins are ligand activated transcription factors whose ligands can range from steroids to retinoids, fatty acids, vitamins, thyroid hormones and other presently unidentified small molecules. These compounds bind to receptors and either up-regulate or down-regulate transcription.

The preferred receptor of the present invention is modification of the glucocorticoid receptor, i.e., the glucocorticoid-mimetic receptor. These receptors can be modified to allow them to bind various ligands whose structure differs from naturally occurring ligands, e.g., RU486. For example, small C-terminal alterations in amino acid sequence, including truncation, result in altered affinity and altered function of the ligand. By screening receptor mutants, receptors can be customized to respond to ligands which do not activate the host cells own receptors.

A person having ordinary skill in the art will recognize, however, that various mutations, for example, a shorter deletion of carboxy terminal amino acids, will be necessary to create useful mutants of certain steroid hormone receptor proteins. Steroid hormone receptors which may be mutated are any of those receptors which comprise the steroid hormone receptor super family, such as receptors including the estrogen, progesterone, glucocorticoid-$\alpha$, glucocorticoid-$\beta$, mineral corticoid, androgen, thyroid hormone, retinoic acid, and Vitamin B3 receptors. Furthermore, DNA encoding for other mutated steroids such as those which are capable of only transrepression or of only transactivation are also within the scope of the above embodiment. Such steroids could be capable of responding to RU486 in order to activate transrepression.

In addition to the above, the present invention can also be used with the following method. Drugs which inhibit the enzyme prostaglandin synthase are important agents in the treatment of arthritis. This is due, in part, to the important role of certain prostaglandin in stimulating the local immune response. Salicylates are widely used drugs but can be administered in limited doses which are often inadequate for severe forms of arthritis.

Gene transfer using the present invention is used to inhibit the action of prostaglandin synthase specifically in affected joints by the expression of an antisense RNA for prostaglandin synthase. The complex formed between the antisense RNA and mRNA for prostaglandin synthase interferes with the proper processing and translation of this mRNA and lowers the levels of this enzyme in treated cells. Alternatively RNA molecules are used for forming a triple helix in regulatory regions of genes expressing enzymes required for prostaglandin synthesis. Alternatively, RNA molecules are identified which bind the active site of enzymes required for prostaglandin synthesis and inhibit this activity.

Alternatively, genes encoding enzymes which alter prostaglandin metabolism can be transferred into the joint. These have an important anti-inflammatory effect by altering the chemical composition or concentration of inflammatory prostaglandin.

Likewise, the present invention is useful for enhancing repair and regeneration of the joints. The regenerative capacity of the joint is limited by the fact that chondrocytes are not capable of remodelling and repairing cartilaginous tissues such as tendons and cartilage. Further, collagen which is produced in response to injury is of a different type lacking the tensile strength of normal collagen. Further, the injury collagen is not remodeled effectively by available collagenase. In addition, inappropriate expression of certain metalloproteinases is a component in the destruction of the joint.

Gene transfer using promoters specific to chondrocytes (i.e., collagen promoters) is used to express different collagens or appropriate collagenase for the purpose of improving the restoration of function in the joints and prevent scar formation.

Gene transfer for these purposes is affected by direct introduction of DNA into the joint space where it comes into contact with chondrocytes and synovial cells. Further, the genes permeate into the environment of the joint where they are taken up by fibroblasts, myoblasts, and other constituents of periarticular tissue.

Direct Delivery to the Lungs

Nucleic acid carriers of the present invention can also be used in reversing or arresting the progression of disease involving the lungs, such as lung cancer. One embodiment involves use of intravenous methods of administration to delivery nucleic acid encoding for a necessary molecule to treat disease in the lung. Nucleic acid carriers which express a necessary protein or RNA can be directly injected into the lungs or blood supply so as to travel directly to the lungs. Furthermore, the use of an aerosol or a liquid in a nebulizer mist can also be used to administer the desired nucleic acid to the lungs. Finally, a dry powder form, such as PVP discussed above, can be used to treat disease in the lung. The dry powder form is delivered by inhalation. These treatments can be used to control or suppress lung cancer or other lung diseases by expression of a particular protein encoded by the nucleic acid chosen.

One skilled in the art would readily appreciate that the present invention is well adapted to carry out the objects and obtain the ends and advantages mentioned, as well as those inherent therein. The nucleic acid carrier systems along with the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

Additional organs, tissues, cavities, cell or cells, spaces for the administration of the molecules mentioned herein may be found in "Nucleic Acid Transporters for Delivery of Nucleic Acids into a Cell"; Smith et al., U.S. patent application Ser. No. 08/484,777, filed Dec. 18, 1995, incorporated herein by reference in its entirety including any drawings.

EXAMPLES

The following examples show synthesis and derivitivation of lipopeptides, coating and enmeshment of nucleic acid, particle sized of peptide-macromolecule complex after enmeshment and condensation, epithelial cell transformation with peptide-macrmolecule complex, and epithelial cell transformation with peptide-macrmolecule complex, the invention is only limited by the claims.

Example 1

Synthesis and Derivitivation of Lipopeptides

Peptide Synthesis—ApoE peptides 148–169, 144–169, 139–169, and 129–169 were synthesized by solid-phase methodology using the programs supplied with the Applied Biosystems 430A peptide synthesizer. The following side chain-protecting groups were used: benzyl ethers for Ser and Thr, benzyl esters for Asp and Glu, dichlorobenzyl ether for Tyr, chlorobenzyloxycarbonyl for Lys, and tosyl for Arg and His. Acylation of the N termini of the peptides was accomplished by N,N-dimethylaminopyridine-catalyzed acylation with palmitic anhydride of the epetidyl resin. The addition of N,N-distearylglycine was accomplished by overnight reaction of the hydroxysuccinimide ester of N,N-distearylglycine with the peptidyl resin in tetrahydofuran/N,N-dimethylformamide (1:1) in the presence of diisopropylethylamine. After synthesis was completed, the resin was washed with N,N-dimethylformamide and methylene chloride and dried in a vacuum desiccator. The peptide was deprotected and cleaved from the resin by treatment at −20° C. for 3 h with anhydrous HF containing 10% anisole and 1% ethanedithiol. The HF was evaporated at −20° C. under vacuum, and the peptide was precipitated with cold ether. The precipitate and resin were washed with ether, and the peptide was dissolved in trifluoroacetic acid. The trifluoroacetic acid was evaporated on a rotary evaporator, and the peptide was precipitated with ether and collected by centrifugation. The precipitated peptide was dissolved in $1_M$ Tris, 6 M guanidinium chloride. The pH was adjusted to 3 with acetic acid, and the peptide was desalted on a Bio-Gel P-2 column (5×50 cm) equilibrated with 5% acetic acid. The peptide-containing fractions were lyophilized, and the peptide was dissolved in 0.1 M ammonium dihydrogen phosphate, 6 M guanidinium chloride, pH 3.0.

Additional information on peptide synthesis and derivatization may be found in Mims et al., Jour. Biol. Chem 269, 20539–47 and "Nucleic Acid Transporters for Delivery of Nucleic Acids into a Cell"; Smith et al., U.S. patent application Ser. No. 08/484,777, filed Dec. 18, 1995, both incorporated herein by reference in their entirety including any drawings or figures.

Example 2

Coating & Enmeshment of Nucleic Acid

An unexpected and surprising result was demonstrated when the peptide detergent micelles were mixed with nucleic acid, rapidly vortexed and diluted approximately 200 fold (below the cmc of the detergent, ~1 mM). Subsequently, the nucleic acid becomes coated with lipophilic peptide and enmeshed; forming a condensed nucleic acid/lipophilic peptide complex while CHAPS detergent monomers can be dialyzed out of the resulting mixture (FIGURE EIGHT).

Example 3

Particle Sized of Peptide-Macromolecule Complex after Enmeshment and Condensation The degree of condensation of the nucleic acid given the treatment of example two is shown as FIGURE NINE. When distearyl-glycyl-apoE-$3^{129-169}$ was added to DNA previously condensed with K8, the particle size increased only ~20%. The addition of JTS-1 increased the particle size another 40%. By contrast, addition of distearyl-glycyl-apoE-$3^{129-169}$ to DNA in the absence of condensing peptide gave a smaller particle, about 60 nm. Condensation and enmeshment with the distearyl-glycyl-apoE-$3^{129-169Q142}$, the mutant peptide, also gave a small, 60 nm monodisperse particle population. When distearyl-glycyl-apoE-$3^{129-169}$ in 10 mM CHAPS was diluted without DNA being present, the resulting vesicles were ~450 nm in diameter. Analysis of distearyl-glycyl-apoE-$3^{129-169}$:DNA complexes subjected to sucrose density gradient centrifugation showed that there was no free DNA after encapsulation. Free DNA in the control remained at the top of the gradient, while the enmeshed-condensed complex was found at the bottom of the centrifugation tube.

Example 4

Epithelial Cell Transformation with Peptide-Macrmolecule Complex

The ability of the formulations of example three to transfect cells was tested in 293 epithelial cells grown in 1 $\mu$g mL$^{-1}$ lovastatin overnight to up-regulate LDL receptors. Neither the galtoselated K8 or JTS-1 were necessary for efficient gene transfer (FIGURE TENc). As expected from the reduced binding of the mutant peptide to the LDL receptor, expression by mutant peptide complexes was about 5% of that observed with the wild-type apoE peptide complexes. We conclude that the diacyl-peptide functions as a condensing agent, an encapsulation agent, a targeting agent and a lytic agent. Apart from the well defined receptor ligand domain, the sequence regions that contain the other functions remain to be elucidated.

The cationic sequence between residues 141–150 of the distearyl-glycyl-apoE-$3^{129-169}$ make the lipophilic peptide comparable to the cationic lipids that have been used successfully for gene delivery to the lungs. We suspect the mechanism of gene delivery is the same for both cationic reagents. Destabilization of the endosomal membrane by the cationic amino acid cluster induces flip-flop of negatively charged phospholipids to offset the charge imbalance, a process that ruptures the endosomal membrane. Interaction of the anionic phospholipids with the cationic lipophilic peptide is stronger than interaction of DNA with the peptide. Consequently, the DNA is released into the cytoplasm for transport by cellular proteins to the nucleus. We expect that short lipophilic peptides containing only one functional sequence can be combined, so that gene delivery in vitro and in vivo can be accomplished by combinations of separate lipophilic peptides. In addition, both commercially available cationic lipid such as DOPE (Dioleoylphosphatidylethanolamine and other lipids including cholesterol, apolipoproteins, fatty acids, lysophospholipids, anionic, neutral and cationic phospholipids, and glycoplipids can be included as additional components in the peptide-macromolecule complex. This example is illustrative and not meant to be limiting.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Those references not previously incorporated herein by reference, including both patent and non-patent references, are expressly incorporated herein by reference for all purposes. Other embodiments are within the following claims.

We claim:

1. A peptide-marcomolecule complex for delivering a marcomolecule into a cell, comprising:

a non-exchangeable lipophilic peptide comprising a delivery peptide associated with a lipid moiety, wherein said delivery peptide portion of said lipophilic peptide is complexed to a macromolecule.

2. The complex of claim 1, wherein said delivery peptide consists of a sequence of amino acids selected from the group consisting of:
STEELRVRLASHLRKLRKRLLRDADDLQKRLAVYQAGAREG, SEQ ID NO:76
KKQLKKQLKKQLKQWK, SEQ ID NO:77
KKSPKKSPKKSPKKSWK, SEQ ID NO:78 and
KRRRRRRRRWR SEQ ID NO:79.

3. The complex of claim 1, wherein said delivery peptide consists of a sequence of amino acids selected from the group consisting of:
KLSKLEKKWSKLEK, SEQ ID NO:80
KLSKLEKKLSKLEKKWSKLEK, SEQ ID NO:81
KSLKKSLKKSLKKSWK, SEQ ID NO:82 and
KSTPPKKKRKVEDPKDFPSELLSA SEQ ID NO:83.

4. The complex of claim 1, wherein said delivery peptide consists of a sequence of amino acids selected from the group consisting of:
KAKKKK-NK- $(CH_2)_2$-SS-$(CH_2)_2$-COKKKKWK, SEQ ID NO:84
KIRRRGKNKVAARTCRQRRTDR, SEQ ID NO:85
KXKKXKKKXKKXKWK, SEQ ID NO:$\xi$(where X is A or S)
KIRRRGKNKAAARTCRERRRSK, SEQ ID NO:87 and
KIRRRGKNKAAQNCRKRKLDQ SEQ ID NO:88.

5. The complex of claim 1, wherein said delivery peptide consists of a sequence of amino acids selected from the group consisting of:
KIRRRGKNKVAAQNCRKRKLET, SEQ ID NO:89
KRRIRREKNKMAAAKCRNRRRELT, SEQ ID NO:90
GRPRAINKHEQEQISRLLEKGHPRQQLAIIFGIGV-STLYRYFPASSIKKRMN, SEQ ID NO:91 and
KSGPRPRGTRGKGRRIRR SEQ ID NO:92.

6. The complex of claim 1, wherein said lipid moiety is a disteryl derivative selected from the group consisting of: (1) N,N-distearyl-glycyl-; (2) $\epsilon$-N,N-distearylglycyl-; and (3) N,N-distearylamidomethyl.

7. The complex of claim 1, wherein said lipid moiety is a dipalmytyl derivative selected from the group consisting of : $N^\alpha$, $N^{\epsilon'}$-dipalmitoyl-, and $N^{\alpha, N\epsilon}$-dipaimitoyl.

8. The complex of claim 1, wherein said complex is capable of binding with a cell surface receptor, lysing an endosome, and targeting the nucleus of said cell.

9. The complex of claim 1 wherein said lipophilic peptide is associated with a surface ligand.

10. The complex of claim 1 wherein said lipophilic peptide is associated with a nuclear ligand.

11. The complex of claim 1 wherein said macromolecule is DNA.

12. The complex of claim 1 wherein said macromolecule is complexed with more than one lipophilic peptides.

13. The complex of claim 1 wherein said macromolecule is complexed with two, three, four, or five lipophilic peptides.

14. The complex of claim 1 wherein said delivery peptide comprises a compound selected from the group consisting of: (1) apoE-$3^{129-169}$; (2) apoE-$3^{139-169}$; and (3) apoE-$3^{129-169}Q142}$.

* * * * *

UNITED STATES PATENT AND TRADEMARK OFFICE
CERTIFICATE OF CORRECTION

PATENT NO.    : 6,344,436 B1                                               Page 1 of 1
DATED         : February 5, 2002
INVENTOR(S)   : Louis C. Smith et al.

It is certified that error appears in the above-identified patent and that said Letters Patent is hereby corrected as shown below:

<u>Column 97,</u>
Line 62, that portion of the sentence reading "SEQ ID NO:ξ" should read -- SEQ ID NO:86 --.

<u>Column 98,</u>
Line 43, that portion of the sentence reading "disteryl" should read -- distearyl --.
Line 47, that portion of the sentence reading "dipalmytyl" should read -- dipalmitoyl --.
Line 48, that portion of the sentence reading "dipaimitoyl" should read -- dipalmitoyl --.

Signed and Sealed this

Seventeenth Day of June, 2003

JAMES E. ROGAN
*Director of the United States Patent and Trademark Office*